(12) United States Patent
Johncock et al.

(10) Patent No.: US 8,440,172 B2
(45) Date of Patent: May 14, 2013

(54) STABLE SOLUBLE SALTS OF PHENYLBENZIMIDAZOLE SULFONIC ACID AT PHS AT OR BELOW 7.0

(75) Inventors: William Johncock, Reinbek (DE); Jürgen Claus, Bevern (DE)

(73) Assignee: Symrise AG, Holzminden (DE)

( * ) Notice: Subject to any disclaimer, the term of this patent is extended or adjusted under 35 U.S.C. 154(b) by 316 days.

(21) Appl. No.: 12/668,152

(22) PCT Filed: Jul. 9, 2007

(86) PCT No.: PCT/EP2007/056995
§ 371 (c)(1),
(2), (4) Date: Feb. 23, 2010

(87) PCT Pub. No.: WO2007/135196
PCT Pub. Date: Nov. 29, 2007

(65) Prior Publication Data
US 2010/0183531 A1    Jul. 22, 2010

(51) Int. Cl.
*A61K 8/49* (2006.01)
*A61K 31/4184* (2006.01)
*A61Q 17/04* (2006.01)
*C07D 235/06* (2006.01)

(52) U.S. Cl.
USPC ............ 424/60; 424/70.9; 424/401; 514/394; 548/310.1

(58) Field of Classification Search .................. None
See application file for complete search history.

(56) References Cited

U.S. PATENT DOCUMENTS

| | | | |
|---|---|---|---|
| 6,153,176 A | 11/2000 | Kaleta et al. | |
| 6,365,167 B1 | 4/2002 | Schutt | |

FOREIGN PATENT DOCUMENTS

| | | | |
|---|---|---|---|
| DE | 33 14 742 A1 | 10/1984 | |
| DE | 19713776 A1 | 10/1998 | |
| DE | 19757826 A1 | 7/1999 | |
| DE | 10055940 A1 | 5/2002 | |
| DE | 101 41 789 A1 | 3/2003 | |
| DE | 10141780 A1 * | 3/2003 | |
| DE | 10141780 A1 | 3/2003 | |
| EP | 0 711 539 A1 | 5/1996 | |
| EP | 0802783 A1 | 10/1997 | |
| EP | 1008593 A1 | 6/2000 | |
| EP | 1 325 735 A2 | 7/2003 | |
| FR | 2 791 564 A1 | 10/2000 | |
| GB | 1 500 390 A | 2/1978 | |
| GB | 2 181 647 A | 4/1987 | |
| JP | 61-030567 A | 2/1986 | |
| KR | 900000847 B1 | 2/1990 | |
| WO | WO-0238537 A1 | 5/2002 | |
| WO | WO-2005107692 A1 | 11/2005 | |
| WO | WO-2006015954 A1 | 2/2006 | |

OTHER PUBLICATIONS

Santo Scalia, Alessandra Molinari, Alberto Casolari, and Andrea Maldotti. Complexation of the sunscreen agent, phenylbenzimidazole sulphonic acid with cyclodextrins: effect on stability and photo-induced free radical formation. European Journal of Pharmaceutical Sciences 22 (2004) 241-249.*
Johncock, W: "Sunscreen Interactions in Formulations", Cosmetics & Toiletries, Wheaton, IL, US, vol. 114, 1999, pp. 75-82.
International Search Report and Written Opinion of International Application No. PCT/EP2007/056995 mailed Mar. 19, 2008.
Creative Developments (Cosmetics) Ltd.; http://www.creative-developments.co.uk/pages/papers12.html, dated 2010.
Paper presented at the UVA Conference, London 2001; J. Woodruff, Creative Developments, UK; "Factors affecting the formulation of sunscreen products".
Communication dated Jan. 23, 2012 issued in corresponding European Application No. 07787271.1.

* cited by examiner

*Primary Examiner* — Frederick Krass
*Assistant Examiner* — Michael P Cohen
(74) *Attorney, Agent, or Firm* — Novak Druce Connolly Bove + Quigg LLP

(57) ABSTRACT

The invention concerns preparations, particularly cosmetic or pharmaceutical/dermatological preparations, containing phenylbenzimidazole sulfonic acid (i.e. 2-phenylbenzimidazole-5-sulfonic acid) neutralised with basic amino acids such as arginine, lysine, ornithine and histidine so that the pH of the preparation can be at or below 7.0 without incurring crystallization of the phenylbenzimidazole sulfonic acid.

14 Claims, 4 Drawing Sheets

STABLE SOLUBLE SALTS OF PHENYLBENZIMIDAZOLE SULFONIC ACID AT PHS AT OR BELOW 7.0

CROSS REFERENCE TO RELATED APPLICATION

Figure 1:
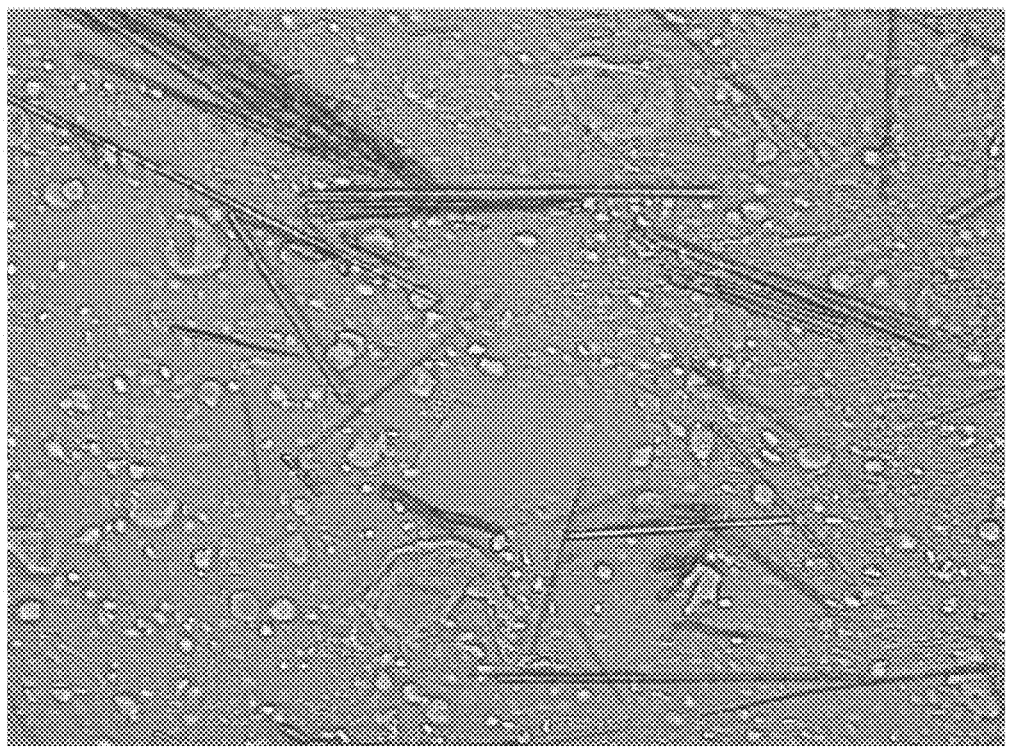

This application is the National Stage of International Application No. PCT/EP2007/056995 filed on Jul. 9, 2007, the entire contents of which is hereby incorporated by reference.

The invention concerns preparations, particularly cosmetic or pharmaceutical/dermatological preparations, containing phenylbenzimidazole sulfonic acid (i.e. 2-phenylbenzimidazole-5-sulfonic acid) neutralised with basic amino acids such as arginine, lysine, ornithine and histidine so that the pH of the preparation can be at or below 7.0 without incurring crystallisation of the phenylbenzimidazole sulfonic acid.

UV rays are classified according to wavelength as UVA rays (320-400 nm, UVA-I: 340-400 nm, UVA-II: 320-340 nm) or UVB rays (280-320 nm). UV rays can cause acute and chronic damage to the skin, the type of damage depending on the wavelength of the radiation. For instance, UVB radiation can cause sunburn (erythema) extending to most severe burning of the skin; reduction in enzyme activities, weakening of the immune system, disturbances of the DNA structure and changes in the cell membrane are also known as harmful effects of UVB rays. UVA rays penetrate into deeper layers of the skin where they can accelerate the aging process of the skin. The shorter wave UVA-II radiation additionally contributes to the development of sunburn. Moreover, UVA radiation can trigger phototoxic or photoallergic skin reactions. Very frequent and unprotected irradiation of the skin by sunlight leads to a loss of skin elasticity and to increased development of wrinkles. In extreme cases, pathogenic changes in the skin extending to skin cancer are observed.

To attenuate these negative effects of UV radiation materials which absorb or reflect UV light, generally called UV absorbers, are used in cosmetic or pharmacological preparations. The UV absorbers are classified as UVA and UVB absorbers depending on the location of their absorption maxima; if a UV absorber absorbs both UVA and UVB, it is referred to as a UV-A/B broadband absorber.

Modern sun protection products contain mixtures of UV filters to absorb both UVB and UVA radiation and there is a lot of research done into finding new UV absorbers but this is very costly, not only for the cost of the R&D effort but for the extensive toxicological testing and registration process required to allow the new filters to be used. It is therefore desirable that the way currently allowed safe and effective UV absorbing materials used for cosmetic or pharmacological preparations be extended. In this respect, one of the most efficient UVB absorbing materials that has been in commercial use since 1934, phenylbenzimidazole sulfonic acid, has a major disadvantage in the way that it is currently formulated. It is very insoluble in water (0.25% w/w); therefore it must be neutralised with a hard base, such as for example but not limited to, sodium hydroxide or potassium hydroxide, or with amines, such as for example but not limited to, triethanolamine or aminomethylpropanol or trishydroxyaminomethane, in order to render the UV filter soluble in a cosmetic or pharmacological preparation. Importantly, if phenylbenzimidazole sulfonic acid is not sufficiently neutralised it will form crystals in the cosmetic or pharmacological preparation (see FIG. 1) rendering it less effective and giving the preparations an unacceptable sandy or grainy feel. Crystal formation starts at pH 7.0; generally, the pH of a cosmetic formulation comprising phenylbenzimidazole sulfonic acid has to remain above 6.8 in order to prevent the free acid from recrystallising (W. Johncock, Cosmetic & Toiletries Magazine, September 1999, pages 75-82). This restriction has prevented the use of phenylbenzimidazole sulfonic acid in formulations with pH at or below 7.0, in particular in the many cosmetic or pharmacological preparations formulations with a pH from 5.5 to 7.0 and 6.0 to 7.0. It is therefore desirable to find a way that allows cosmetic or pharmacological preparations to be formulated with phenylbenzimidazole sulfonic acid at a pH of or below 7.0 in order to broaden its application.

U.S. Pat. No. 6,153,176 indicated that low pH formulations containing phenylbenzimidazole sulfonic acid could be prepared in which 75% to 95% of the acid remains in its non-neutralised form, but the authors did not indicate whether the acids recrystallised or not. In the formulation examples given in the patent we found that the acid did in fact recrystallise.

Surprisingly and unexpectedly we have found that when basic amino acid, preferably, but not restricted to, arginine, histidine, ornithine and lysine or their derivatives are used to neutralise phenylbenzimidazole sulfonic acid, the pH can be taken to below 7.0 and down to as low as 5.5, wherein best stabilisation of phenylbenzimidazole sulfonic acid in cosmetic compositions is achieved by a pH down to 6.0 without causing recrystallisation of the phenylbenzimidazole sulfonic acid. Stabilisation in the meaning of the present invention is achieved when a formulation comprising phenylbenzimidazole sulfonic acid (all phenylbenzimidazole sulfonic acid being originally in non-crystalline, preferably dissolved, form) is free from phenylbenzimidazole sulfonic acid crystals at least after storage of the formulation at 20° C. for two days or more, preferably for five days or more. The isoelectric point of other amino acids (see table 1) preclude the formation of salts when simply mixed with phenylbenzimidazole sulfonic acid.

TABLE 1

Isoelectric points and pK values of some preferred basic amino acids.

| Amino Acid | Isoelectric Point | $pK_1$ ($\alpha$-COOH) | $pK_2$ ($\alpha$-$^+NH_3$) |
|---|---|---|---|
| Histidine | 7.60 | 1.80 | 9.33 |
| Lysine | 9.60 | 2.16 | 9.06 |
| Arginine | 10.76 | 1.82 | 8.99 |

EP 1 325 735 teaches the use of the basic amino acid arginine and its derivatives as a precursor of nitrogen monoxide (NO) to promote melanogenesis in photoprotective skin care products. It does not teach the use of arginine or its derivatives as a suitable base to neutralise phenylbenzimidazole sulfonic acid to obtain a pH below 7.0.

EP 0 802 783 teaches the use of the combination of arginine or its salts, amides or esters with folic acid, urea and antioxidants with or without the presence of UV absorbing materials for the prophylaxis and/or treatment of dry and scaly skin and of aged skin, in particular of skin damaged by endogenous or chronological aging. It does not teach the use of arginine or its derivatives as a suitable base to neutralise phenylbenzimidazole sulfonic acid to obtain a pH below 7.0.

FF 2 791 564 teaches that in contrast to the use of azelaic acid alone, when azelaic acid is neutralised with arginine or lysine to a pH between 5 and 7 it obtains antioxidative properties and is useful to protect the skin against UV induced oxidative stress. It does not teach the use of arginine or its derivatives as a suitable base to neutralise phenylbenzimidazole sulfonic acid to obtain a pH below 7.0.

U.S. Pat. No. 6,365,167 teaches the use of arginine neutralised para aminobenzoic acid (PABA) to treat wounds, lacerations, burns and ulcers of human and animal skin. The use of arginine is not to improve the solubility of PABA and in particular the patent does not teach the use of arginine to render salts of PABA soluble at pHs below 7.0, nor does. it teach the use of arginine or its derivatives as a suitable base to neutralise phenylbenzimidazole sulfonic acid to obtain a pH below 7.0.

KR 900000847 B teaches the use of arginine with p-aminobenzoate, salicylate, cinnamate and benzophenonone UV filters but not phenylbenzimidazole sulfonic acid, to control the colour of cosmetic compositions when exposed to UV light. The pH of these compositions is controlled by the use of either citric acid or triethanolamine to pH 5.0 to 8.0. Arginine is not used as a neutralising agent in this case.

EP 0 711 539 teaches the use of amines including triethanolamine and amino acids to neutralise salicylic acid and its derivatives to render them more soluble in a formulation and as alternative emulsifiers to traditional ones used. The document does not indicate that the use of basic amino acids improves the solubility of salicylic acid and its derivatives over other amines such as triethanolamine and trishydroxymethylaminomethane, though they do indicate that the emulsion is more fine when lysine is used as the base. The invention does not teach that the use of basic amino acids would prevent the recystallisation of phenylbenzimidazolesulfonic acid.

GB 2 181 647 teaches the use of arginine and lysine in association with fatty to produce substances which have anti irritation, antioxidant and emulsification properties. It does not teach that the use of basic amino acids would prevent the recystallisation of phenylbenzimidazolesulfonic acid.

JP 61-030567 teaches the use of basic amino acids, lysine, arginine, ornithine, histidine to stabilise urea against decomposition, it does not teach that the use of basic amino acids would prevent the recystallisation of phenylbenzimidazolesulfonic acid.

DE 101 41 789 teaches the use of histidine in cosmetic formulations to prevent loss of urocanic acid from the skin. The patent mentions that the formulations can contain UVA and UVB filters including sulfonated water soluble salts such as the sodium potassium or triethanolamine salts of phenylbenzimidazole sulfonic acid. Histidine is not used in the formulations as a neutralisation agent in the formulation since the amounts of histidine used (0.7 to 0.4 equivalents) is far below those to neutralise phenylbenzimdazole sulfonic acid to a pH of 6.0 to 7.0. The only formulation example in the patent which indicate a pH is indicated is example 9 which does not contain any UV filter. The patent does not teach the use of histidine to prevent the recystallisation of phenylbenzimidazole sulfonic acid at pHs below 7.0.

GB 1 500 390 describes the use of basic amino acids to neutralise aqueous solutions of vinylether/maleic anhydride polymers to a pH of 3 to 9 to avoid skin irritation associated with other bases such as mineral bases or triethanolamine, it does not teach that the use of basic amino acids would prevent the recystallisation of phenylbenzimidazolesulfonic acid.

DE 197 13 776 A1 discloses compositions comprising (a) one or more UV-filters comprising one or more sulfonic acids or sulfonated groups and (b) basic amino acids. Such compositions have an increased SPF (sun protection factor), improved water-resistance and particularly a higher stability in the presence of sulfonated UV-filters (in particular in O/W-emulsions); the use of basic amino acids for achieving a higher stability of emulsions is also disclosed, in particular in the presence of sulfonated UV-filters.

For comparison we prepared the emulsions of examples 1, 3 and 4 of DE 197 13 776. Emulsions of examples 1 and 3 of DE 197 13 776 as such were stable. The following further observations were made:

example 1: pH=5.9; phenylbenzimidazole sulfonic acid had not been dissolved completely; crystals of phenylbenzimidazole sulfonic acid were present even when heating the formulation to 95° C.;

example 3: pH=5.4; phenylbenzimidazole sulfonic acid recrystallised out of the emulsion after two days at 20° C.;

example 4: pH=4.0 (at 83° C.), the water phase separated, recystallisation of phenylbenzimidazole sulfonic acid was observed Thus, DE 197 13 776 A1 does not teach a reliable way to stabilise phenylbenzimidazole sulfonic acid. Surprisingly, it has now been found that basic amino acids can be used as a neutralisation agent in cosmetics to partially neutralise phenylbenzimidazole sulfonic acids to pH-values in the range of from 5.5 to 7.0 and particularly from 6.0 to 7.0 (measured at 25° C.), which prevents the expected recystallisation of phenylbenzimidazole sulfonic acid at these pHs.

The present invention relates to cosmetic formulations having a pH-value in the range of from 5.5 to 7.0, preferably from 6.0 to or below 7.0, and more preferably in the range of 6.0 to 6.8, comprising (i) 1-8 wt.-%, preferably 1-5, wt.-%, of phenylbenzimidazole sulfonic acid, and (ii) a total of at least 50 wt.-%, preferably 60-150 wt.-%, of one or more basic amino acids, based on the amount of phenylbenzimidazole sulfonic acid (i).

Preferably, the one or more basic amino acid are selected from the group consisting of arginine, lysine, histidine and ornithine.

Preferably the pH-value of a cosmetic, dermatologic or pharmaceutical formulation according to the invention is in the following ranges:

when arginine is comprised in the formulation: pH of 6.0 to below 7.0, preferably to 6.8;

when lysine is comprised in the formulation: pH of 6.2 to below 7.0, preferably 6.3 to below 7.0, and more preferably 6.3 to 6.8;

when histidine is comprised in the formulation: pH of 6.0 to below 7.0, preferably to 6.8; and when ornithine is comprised in the formulation: pH of 6.2 to below 7.0, preferably to 6.8.

In one preferred embodiment, cosmetic and/or pharmaceutical preparations of the invention comprise phenylbenzimidazole sulfonic acid neutralised with basic amino acids as described above in combination with one or more further UV absorbers, preferably a total fraction of UV absorbers in the range from 0.1% to 40% by weight, more preferably in the range from 0.2% to 30% by weight and more preferably in the range 0.5% to 20% by weight, based on the total weight of the preparation.

In a further preferred embodiment a cosmetic and/or pharmaceutical preparation of the invention, especially a dermatologically active preparation, comprises a total amount of UV filters and/or inorganic pigments such that the preparation of the invention has a sun protection factor of greater than or equal to 2 (preferably greater than or equal to 5). These sunscreens are suitable for protecting skin and hair.

Further suitable photoprotective agents (UV absorbers) are, for example, organic UV absorbers from the class of 4-aminobenzoic acid and derivatives, salicylic acid derivatives, benzophenone derivatives, dibenzoylmethane derivatives, diphenylacrylates, 3-imidazol-4-ylacrylic acid and its esters, benzofuran derivatives, benzylidenemalonate derivatives, polymeric UV absorbers containing one or more organosilicon radicals, cinnamic acid derivatives, camphor derivatives, trianilino-s-triazine derivatives, 2-hydroxyphenylbenzotriazole derivatives, phenyl dibenzimidazolesulphonic acid derivatives and salts thereof, menthyl anthranilate, benzotriazole derivatives, indole derivatives.

The UV absorbers specified below, which can be used additionally for the purposes of the present invention, are preferred, but of course are not limiting.

Such preferred UV filters are as follows:
UV-B filters such as, for example:
p-aminobenzoic acid
ethyl p-aminobenzoate (25 mol) ethoxylated
2-ethylhexyl p-dimethylaminobenzoate
ethyl p-aminobenzoate (2 mol) N-propoxylated
glycerol p-aminobenzoate
homomethyl salicylate (homosalate) (Neo Heliopan®HMS)
2-ethylhexyl salicylate (Neo Heliopan®OS)
triethanolamine salicylate (Neo Heliopan® TS)
4-isopropylbenzyl salicylate
menthyl anthranilate (Neo Heliopan®MA)
ethyl diisopropylcinnamate
2-ethylhexyl p-methoxycinnamate (Neo Heliopan®AV)
methyl diisopropylcinnamate
isoamyl p-methoxycinnamate (Neo Heliopan®E 1000)
p-methoxycinnamic acid diethanolamine salt
isopropyl p-methoxycinnamate
  3-(4'-trimethylammonium)benzylidenebornan-2-one methyl sulphate
β-imidazole-4(5)-acrylic acid (urocanic acid)
3-(4'-sulpho)benzylidenebornan-2-one and salts
3-(4'-methylbenzylidene)-d,l-camphor (Neo Heliopan®MBC)
3-benzylidene-d,l-camphor
N-[(2 and 4)-[2-(oxoborn-3-ylidene)methyl]benzyl]acrylamide polymer
4,4'-[(6-[4-(1,1-dimethyl)aminocarbonyl)phenylamino]-1,3,5-triazine-2,4-diyl)diimino]bis(benzoic acid 2-ethylhexyl ester) (Uvasorb®HEB)
benzylidenemalonate-polysiloxane (Parsol®SLX)
glyceryl ethylhexanoate dimethoxycinnamate
dipropylene glycol salicylate
tris(2-ethylhexyl) 4,4',4''-(1,3,5-triazine-2,4,6-triyltriimino)tribenzoate (Uvinul®T150)
Benzylidene butyrolactones described in EP 1008593
Benzylidene-β-dicarbonyl compounds described in WO 2005/107692
Broadband filters such as, for example:
2-ethylhexyl 2-cyano-3,3-diphenylacrylate (Neo Heliopan®303)
ethyl 2-cyano-3,3'-diphenylacrylate
hydroxy-4-methoxybenzophenone (Benzophenone-3, Oxybenzone) (Neo Heliopan® BB)
2-hydroxy-4-methoxybenzophenone-5-sulphonic acid (benzophenone-4, sulisobenzone) and its salts
disodium 2,2'-dihydroxy-4,4'-dimethoxy-5,5'-disulphobenzophenone
phenol, -(2H-benzotriazol-2-yl-4-methyl-6-(2-methyl-3-(1,3,3,3-tetramethyl-1-(trimethylsilyl)oxy)disiloxanyl)propyl), (Mexoryl®XL)
2,2'-methylenebis(6-(2H-benztriazol-2-yl)-4-1,1,3,3-tetramethylbutyl)-phenol), (Tinosorb®M)
2,4-bis[4-(2-ethylhexyloxy)-2-hydroxyphenyl]-1,3,5-triazine
2,4-bis[{(4-(2-ethylhexyloxy)-2-hydroxy}phenyl]-6-(4-methoxyphenyl)-1,3,5-triazine, (Tinosorb®S)
2,4-bis[{(4-(3-sulphonato)-2-hydroxypropyloxy)-2-hydroxy}phenyl]-6-(4-methoxyphenyl)-1,3,5-triazine sodium salt
2,4-bis[{(3-(2-propyloxy)-2-hydroxypropyloxy)-2-hydroxy}phenyl]-6-(4-methoxyphenyl)-1,3,5-triazine
2,4-bis[{4-(2-ethylhexyloxy)-2-hydroxy}phenyl]-6-[4-(2-methoxyethyl-carbonyl)phenylamino]-1,3,5-triazine
2,4-bis[{4-(3-(2-propyloxy)-2-hydroxypropyloxy)-2-hydroxy}phenyl]-6-[4-(2-ethylcarboxyl)phenylamino]-1,3,5-triazine
2,4-bis[{4-(2-ethylhexyloxy)-2-hydroxy}phenyl]-6-(1-methylpyrrol-2-yl)-1,3,5-triazine
2,4-bis[{4-tris(trimethylsiloxysilylpropyloxy)-2-hydroxy}phenyl]-6-(4-methoxyphenyl)-1,3,5-triazine
2,4-bis[{4-(2"-methylpropenyloxy)-2-hydroxy}phenyl]-6-(4-methoxyphenyl)-1,3,5-triazine
2,4-bis[{4-(1',1',1',3',5',5',5'-heptamethylsiloxy-2"-methylpropyloxy)-2-hydroxy}phenyl]-6-(4-methoxyphenyl)-1,3,5-triazine.
UV-A filters such as, for example:
terephthalylidenedibornanesulphonic acid and salts (Mexoryl®SX)
4-t-butyl-4'-methoxydibenzoylmethane (avobenzone) (Neo Heliopan®357)
2,2'-(1,4-phenylene)bis(1H-benzimidazole-4,6-disulphonic acid), monosodium salt (Neo Heliopan®AP)
hexyl 2-(4-diethylamino-2-hydroxybenzoyl)benzoate (Uvinul® A Plus)
4-isopropyldibenzoylmethane
menthyl anthranilate (Neo Heliopan®MA)
indanylidene compounds as described in DE 100 55 940 or WO 02/38537.
Benzoylcinnamyl nitriles described in WO 2006/015954
UV absorbers particularly suitable for combination are as follows:
p-aminobenzoic acid
3-(4'-trimethylammonium)benzylidenebornan-2-one methyl sulphate
homomethyl salicylate (Neo Heliopan®HMS)
terephthalylidenedibornanesulphonic acid and salts (Mexoryl®SX)
4-tert-butyl-4'-methoxydibenzoylmethane (Neo Heliopan®357)
3-(4'-sulpho)benzylidenebornan-2-one and salts
2-ethylhexyl 2-cyano-3,3-diphenylacrylate (Neo Heliopan®303)
N-[(2 and 4)-[2-(oxoborn-3-ylidene)methyl]benzyl]acrylamide polymer
2-ethylhexyl p-methoxycinnamate (Neo Heliopan®AV)
ethyl p-aminobenzoate (25 mol) ethoxylated
isoamyl p-methoxycinnamate (Neo Heliopan®E1000)
2,4,6-trianilino(p-carbo-2'-ethylhexyl-1'-oxy)-1,3,5-triazine (Uvinul®T150)
phenol, 2-(2H-benzotriazol-2-yl)-4-methyl-6-(2-methyl-3-(1,3,3,3-tetramethyl-1-(trimethylsilyl)oxy)disiloxanyl)propyl), (Mexoryl®XL)
4,4'-[(6-[4-(1,1-dimethyl)aminocarbonyl)phenylamino]-1,3,5-triazin-2,4-diyl)-diimino]bis(benzoic acid 2-ethylhexyl ester), (Uvasorb HEB)
3-(4'-methylbenzylidene)-d,l-camphor (Neo Helipan®MBC)
3-benzylidenecamphor 2-ethylhexyl salicylate (Neo Helipan®OS)
2-ethylhexyl 4-dimethylaminobenzoate (Padimate O)
hydroxy-4-methoxybenzophenone (Benzophenone-3, Oxybenzone) (Neo Heliopan® BB)
2-hydroxy-4-methoxybenzophenone-5-sulphonic acid (benzophenone-4, sulisobenzone) and its salts
2,2'-methylenebis(6-(2H-benzotriazol-2-yl)-4-1,1,3,3-tetramethylbutyl)-phenol), (Tinosorb®M)
phenylenebisbenzimidazyltetrasulphonic acid disodium salt (Neo Heliopan®AP)
2,4-bis[{(4-(2-ethylhexyloxy)-2-hydroxy}phenyl]-6-(4-methoxyphenyl)-1,3,5-triazine, (Tinosorb®S)
benzylidenemalonate-polysiloxane (Parsol®SLX)
menthyl anthranilate (Neo Heliopan®MA)
hexyl 2-(4-diethylamino-2-hydroxybenzoyl)benzoate (Uvinul® A Plus)
indanylidene compounds as described in DE 100 55 940 (WO 02/38537)
Benzoylcinnamyl nitriles described in WO 2006/015954
Benzylidene butyrolactones described in EP 1008593
Benzylidene-β-dicarbonyl compounds described in WO 2005/107692

It is possible, furthermore, to use particulate UV filters or inorganic pigments, which if desired may have been rendered hydrophobic, such as the oxides of titanium ($TiO_2$), of zinc (ZnO), of iron ($Fe_2O_3$), of zirconium ($ZrO_2$), of silicon ($SiO_2$), of manganese (z.B. MnO), of aluminium ($Al_2O_3$), of cerium (e.g. $Ce_2O_3$) and/or mixtures.

The total amount of all sulfonated water soluble UV filters in the cosmetic or dermatological formulation, for example but not limited to phenylbenzimidazole sulfonic acid neutralised with basic amino acids alone or in combination with phenylenebisbenzimidazyltetrasulphonic acid disodium salt and or 2-hydroxy-4-methoxybenzophenone-5-sulphonic acid and/or terephthalylidenedibornanesulphonic acid, and/or 3-(4'-trimethylammonium)benzylidenebornan-2-one methyl sulphate, and/or 3-(4'-sulpho)benzylidenebornan-2-one, and their salts (amine, hard base or amino acid) are in the range of 0.1 to 15.0 wt.-% and more particularly in the range from 0.5 to 10.0% and most particularly in the range of 1.0 to 8.0% of the total formulation.

The amount of phenylenebisbenzimidazyltetrasulphonic acid disodium salt and its salts (amine, hard base or amino acid) used in the cosmetic or dermatological formulation containing phenylbenzimidazole sulfonic acid neutralised with basic amino acids is in the range of 0.1 to 10.0 wt.-%, preferably in the range from 0.3 to 8% and most preferably in the range from 0.5 to 5.0% of the total formulation.

The amount of terephthalylidenedibornanesulphonic acid (Mexoryl®SX) and its salts (amine, hard base or amino acid) used in the cosmetic or dermatological formulation containing phenylbenzimidazole sulfonic acid neutralised with basic amino acids is in the range of 0.1 to 10.0 wt.-%, preferably in the range from 0.3 to 8% and most preferably in the range from 0.5 to 5.0% of the total formulation.

The amount of Benzophenone-4 and its salts (amine, hard base or amino acid) used in the cosmetic or dermatological formulation containing phenylbenzimidazole sulfonic acid neutralised with basic amino acids is in the range of 0.1 to 10.0 wt.-%, preferably in the range from 0.3 to 8% and most preferably in the range from 0.5 to 5.0% of the total formulation.

The total amount of oil soluble UV filters that may be used in a cosmetic or dermatological formulation containing phenylbenzimidazole sulfonic acid neutralised with basic amino acids, for example but not limited to (2-ethylhexyl) 4,4',4"-(1,3,5-triazine-2,4,6-triyltriimino)tribenzoate and/or -tert-butyl-4'-methoxydibenzoylmethane, and/or 2-ethylhexyl 4-dimethylaminobenzoate, and/or Mexoryl®XL and/or Uvasorb®HEB and/or Tinosorb®S and/or Benzophenone-3 and/or Parsol®SLX and/or Neo Heliopan®MA, and/or isoamyl p-methoxycinnamate, and/or 2-ethylhexyl salicylate, and/or homosalate, and/or ethylhexyl methoxycinnamate, and/or octocrylene, and/or Uvinul® A Plus, and/or 3-(4'-methylbenzylidene)-d,l-camphor are in the range of 0.1 to 30%, particularly in the range of 0.5 to 25%, most particularly in the range of 1 to 20% of the total formulation.

The amount of Ethylhexyl methoxycinnamate used in the cosmetic or dermatological formulation containing phenylbenzimidazole sulfonic acid neutralised with basic amino acids is in the range of 0.1 to 20.0%, preferably in the range from 0.3 to 15% and most preferably in the range from 0.5 to 10.0% of the total formulation.

The amount of Isoamyl p-methoxycinnamate used in the cosmetic or dermatological formulation containing phenylbenzimidazole sulfonic acid neutralised with basic amino acids is in the range of 0.1 to 20.0%, preferably in the range from 0.3 to 15% and most preferably in the range from 0.5 to 10.0% of the total formulation.

The amount of Octocrylene used in the cosmetic or dermatological formulation containing phenylbenzimidazole sulfonic acid neutralised with basic amino acids is in the range of 0.1 to 20.0%, preferably in the range from 0.3 to 15% and most preferably in the range from 0.5 to 10.0% of the total formulation.

The amount of salicylate esters used in the cosmetic or dermatological formulation containing phenylbenzimidazole sulfonic acid neutralised with basic amino acids is in the range of 0.1 to 20.0%, preferably in the range from 0.3 to 15% and most preferably in the range from 0.5 to 10.0% of the total formulation. When Ethylhexyl salicylate is chosen as the UV filter, it is advantageous that its total amount ranges from 0.1 to 5.0% of the formulation and when Homosalate is chosen as the UV filter it is advantageous that its total amount ranges from 0.1 to 15.0% of the formulation The amount of Butyl methoxydibenzoylmethane used in the cosmetic or dermatological formulation containing phenylbenzimidazole sulfonic acid neutralised with basic amino acids is in the range of 0.1 to 10.0%, preferably in the range from 0.3 to 7.0% and most preferably in the range from 0.5 to 5.0% of the total formulation.

The amount of Uvinul® A Plus used in the cosmetic or dermatological formulation containing phenylbenzimidazole sulfonic acid neutralised with basic amino acids is in the range of 0.1 to 10.0%, preferably in the range from 0.3 to 7.0% and most preferably in the range from 0.5 to 5.0% of the total formulation.

The amount of Tinosorb®S used in the cosmetic or dermatological formulation containing phenylbenzimidazole sulfonic acid neutralised with basic amino acids is in the range of 0.1 to 10.0%, preferably in the range from 0.3 to 7.0% and most preferably in the range from 0.5 to 5.0% of the total formulation.

The amount of Uvasorb HEB used in the cosmetic or dermatological formulation containing phenylbenzimidazole sulfonic acid neutralised with basic amino acids is in the range of 0.1 to 10.0%, preferably in the range from 0.3 to 7.0% and most preferably in the range from 0.5 to 5.0% of the total formulation.

The amount of Uvinul® T-150 used in the cosmetic or dermatological formulation containing phenylbenzimidazole sulfonic acid neutralised with basic amino acids is in the range of 0.1 to 10.0%, preferably in the range from 0.3 to 7.0% and most preferably in the range from 0.5 to 5.0% of the total formulation.

The total amount of oil microfine organic and/or inorganic pigments, for example but not limited to triazine derivatives and/or Zinc Oxide (coated and un-coated), and/or titanium dioxide (coated or uncoated) that may be used in a cosmetic or dermatological formulation containing phenylbenzimidazole sulfonic acid neutralised with basic amino acids is in the range of 0.1 to 20.0%, preferably in the range from 0.3 to 15% and more preferably in the range from 0.5 to 10.0% and most preferably in the range from 0.75% to 7.5%. When titanium dioxide is chosen as the UV filter, it is advantageous that its total amount ranges from 0.1% to 10.0% of the formulation. When Zinc Oxide is chosen as the UV filter it is advantageous that its total amount ranges from 0.1% to 10.0% of the formulation and when one or more triazine organic pigment(s) are chosen it is advantageous that its total amount ranges from 0.1% to 10.0% of the formulation.

Combining phenylbenzimidazole sulfonic acid neutralised with basic amino acids with other UV filters, for example with the UV filters listed above and particularly the UV filters listed as "particularly suitable for combination", but not limited to these, leads to synergistic effects in the degree of protection offered against UVB and UVA radiation as determined by measurements to determine sun protection factors against UVA and/or UVB radiation.

The invention thus also provides the teaching that combining phenylbenzimidazole sulfonic acid neutralised with basic amino acids with individual or any desired mixtures of any of the UV filters listed above as well as any from the allowed UV filters for use in sun protection products presently legislated in:

USA: by the Food and Drug Administration (FDA). published in the Monograph for Sunscreen Drug Products for Over-The-Counter Human Use.

Europe: by the Cosmetics Directive 76/768 EEC of the Council of European Communities published in the in the Official Journal of the European Communities.

Japan: in the positive list of allowed UV filters in the publication of the cosmetic criteria by the Ministry of Health and Welfare (MHW).

Australia: in the positive list of allowed UV filters published by the Australian Therapeutic Goods Administration in the Australian Register of Therapeutic Goods (ARTG).

leads to synergistic protective effects against UVA and/or UVB radiation.

Combining phenylbenzimidazole sulfonic acid neutralised with basic amino acids with other UV filters with filters that absorb in the UVA range leads to broad band UV protection cosmetic and dermatological formulations.

Improved photostable cosmetic and dermatological formulations can also be formulated with phenylbenzimidazole sulfonic acid neutralised with basic amino acids with other UV filters, either alone or with other UV filters as listed above.

The cosmetic and/or dermatological formulations according to the present invention can have the customary composition and can be used for cosmetic and/or dermatological sun protection, and also for the treatment, care and cleansing of the skin and/or of the hair and as a make-up product in decorative cosmetics. Accordingly, the preparations according to the present invention can, depending on their formulation, be used, for example, as skin protection cream, cleansing milk, sunscreen lotion, nourishing cream, day cream or night cream. The preparations according to the present invention can, depending on their formulation, also be used for example, in hair care compositions such as shampoos, conditioners, 2 in 1 formulations, anti-dandruff shampoos, hair tonics, hair lotions, hair rinses, styling products, sprays, etc. In some instances, it is possible and advantageous to use the preparations according to the present invention as bases for pharmaceutical formulations. Preference is given, in particular, to those cosmetic and dermatological preparations in the form of a skin care, hair care or make-up product. Typical embodiments are creams, gels e.g. but not limited to hydrogels, hydrodispersion gels, oil gels; lotions, alcoholic and aqueous/alcoholic solutions, emulsions in their various forms for example but not limited to oil in water (O/W), water in oil (W/O), mixed emulsions, PIT emulsions, Pickering emulsions, microemulsions, nano-emulsions; aerosol foams, non-aerosol foams, aerosols sprays, non-aerosol sprays, pump sprays, serums, roll-ons, pastes, balsams, or stick preparations. These compositions may also comprise, as further auxiliaries and additives, mild surfactants, co-emulsifiers, superfatting agents, pearlescent waxes, bodying agents, thickeners, polymers, silicone compounds, fats, waxes, stabilisers, biogenic active ingredients, deodorant active ingredients, anti-dandruff agents, film formers, swelling agents, hydrotropic agents, preservatives, insect repellants, tanning agents, artificial self-tanning agents (e.g. dihydroxyacetone), stabilisers, perfume oils, dyes, antimicrobial agents, aqueous and non-aqueous plant extracts and the like.

For use, the cosmetic and dermatological preparations according to the present invention are applied to the skin and/or the hair in a sufficient amount in the manner customary for cosmetics or pharmacological and dermatological preparations.

More preference is given to those cosmetic and dermatological preparations in the form of a cosmetic composition for the protection of the skin and hair. Advantageously, in addition to phenylbenzimidazole sulfonic acid neutralised with basic amino acids used according to the present invention, these can contain at least one inorganic pigment, preferably an inorganic micropigment.

The cosmetic and dermatological preparations according to the present invention can comprise cosmetic auxiliaries, as are customarily used in such preparations, e.g. preservatives, bactericides, perfumes, antifoams, dyes, pigments which have a coloring action, thickeners, moisturizers and/or humectants, fats, oils, waxes or other customary constituents of a cosmetic or dermatological formulation, such as alcohols, polyols, polymers, foam stabilisers, electrolytes, organic solvents or silicone derivatives. The amounts of cosmetic or dermatological auxiliaries and carrier substances and perfume which can be used in each case can be determined easily by the person skilled in the art by simple trial and error, depending on the nature of the product in question.

Preferred embodiments of the cosmetic and/or pharmaceutical, especially dermatological preparations of the invention may also comprise anionic, cationic, nonionic and/or amphoteric surfactants. Surfactants are amphiphilic substances which can dissolve organic, nonpolar substances in water. In this context, the hydrophilic components of a surfactant molecule are usually polar functional groups, for example —COO$^-$, —OSO$_3^{2-}$, —SO$_3^-$, while the hydrophobic parts as a rule are nonpolar hydrocarbon radicals. Surfactants are in general classified according to the nature and charge of the hydrophilic molecular moiety. A distinction can be made between four groups here:

anionic surfactants,
cationic surfactants,
amphoteric surfactants and
nonionic surfactants.

Anionic surfactants as a rule contain carboxylate, sulphate or sulphonate groups as functional groups. In aqueous solution, they form negatively charged organic ions in an acid or neutral medium. Cationic surfactants are almost exclusively characterised by the presence of a quaternary ammonium group. In aqueous solution, they form positively charged organic ions in an acid or neutral medium. Amphoteric surfactants contain both anionic and cationic groups and accordingly behave like anionic or cationic surfactants in aqueous solution, depending on the pH. In a strongly acid medium they have a positive charge, and in an alkaline medium a negative charge. On the other hand, they are zwitterionic in the neutral pH range. Polyether chains are typical of nonionic surfactants. Nonionic surfactants do not form ions in an aqueous medium.

A. Anionic Surfactants

Anionic surfactants which are advantageously used are acylamino acids (and salts thereof), such as:
- acyl glutamates, for example sodium acyl glutamate, di-TEA-palmitoyl aspartate and sodium caprylic/capric glutamate,
- acyl peptides, for example palmitoyl hydrolysed milk protein, sodium cocoyl hydrolysed soya protein and sodium/potassium cocoyl hydrolysed collagen,
- sarcosinates, for example myristoyl sarcosine, TEA-lauroyl sarcosinate, sodium lauroyl sarcosinate and sodium cocoyl sarcosinate,
- taurates, for example sodium lauroyl taurate and sodium methylcocoyl taurate,
- acyl lactylates, lauroyl lactylate, caproyl lactylate
- alaninates
- carboxylic acids and derivatives, such as for example:
- TEA stearate, Glyceryl stearates, PEG glyceryl stearates
- lauric acid, aluminium stearate, magnesium alkanolate and zinc undecylenate,
- ester-carboxylic acids, for example calcium stearoyl lactylate, laureth-6 citrate and sodium PEG-4 lauramide carboxylate, glyceryl stearates, glyceryloleylstearates, glyceryl citrates, glyceryl oleyl citrates,
- ether-carboxylic acids, for example sodium laureth-13 carboxylate and sodium PEG-6 cocamide carboxylate,
- Glucoside esters, such as for example
- cetearyl glucoside, lauryl glucoside
- phosphoric acid esters and salts, such as, for example:
- cetyl phosphate (mono, di cetyl and their mixtures), Potassium cetyl phosphate, (mono, di cetyl and their mixtures), DEA cetyl phosphate (mono, di cetyl and their mixtures), DEA-oleth-10 phosphate and dilaureth-4 phosphate,
- sulphonic acids and salts, such as
- acyl isethionates, e.g. sodium/ammonium cocoyl isethionate,
- alkylarylsulphonates,
- alkylsulphonates, for example sodium coco-monoglyceride sulphate, sodium C12-14 olefinsulphonate, sodium lauryl sulphoacetate and magnesium PEG-3 cocamide sulphate,
- sulphosuccinates, for example dioctyl sodium sulphosuccinate, disodium laureth-sulphosuccinate, disodium laurylsulphosuccinate and disodium undecylenamido-MEA-sulphosuccinate and
- sulphuric acid esters, such as:
- alkyl ether sulphate, for example sodium, ammonium, magnesium, MIPA, TIPA laureth sulphate, sodium myreth sulphate and sodium C12-13 pareth sulphate,
- alkyl sulphates, for example sodium, ammonium and TEA lauryl sulphate.

B. Cationic Surfactants

Cationic surfactants which are advantageously used are
- alkylamines,
- alkylimidazoles,
- ethoxylated amines,
- quaternary surfactants,
- $RNH_2CH_2CH_2COO^-$ (at pH=7)
- $RNHCH_2CH_2COO^-$ $B^+$ (at pH=12) $B^+$=any desired cation, e.g. $Na^+$ and
- ester quats.

Quaternary surfactants contain at least one N atom which is covalently bonded to 4 alkyl or aryl groups. This leads to a positive charge, independently of the pH. Alkylbetaine, alkylamidopropylbetaine and alkylamidopropylhydroxysulphaine are advantageous. The cationic surfactants used can further preferably be chosen from the group consisting of quaternary ammonium compounds, in particular benzyltrialkylammonium chlorides or bromides, such as, for example, benzyldimethylstearylammonium chloride, and also alkyltrialkylammonium salts, for example cetyltrimethylammonium chloride or bromide, alkyldimethylhydroxyethylammonium chlorides or bromides, dialkyldimethylammonium chlorides or bromides, alkylamideethyltrimethylammonium ether sulphates, alkylpyridinium salts, for example lauryl- or cetylpyridinium chloride, imidazoline derivatives and compounds having a cationic character, such as amine oxides, for example alkyldimethylamine oxides or alkylaminoethyldimethylamine oxides. Cetyltrimethyl-ammonium salts in particular are advantageously used.

C. Amphoteric Surfactants

Amphoteric surfactants which are advantageously to be used are
- acyl/dialkylethylenediamine, for example sodium acylamphoacetate, disodium acylamphodipropionate, disodium alkylamphodiacetate, sodium acylamphohydroxypropylsulphonate, disodium acylamphodiacetate and sodium acylamphopropionate,
- N-alkylamino acids, for example aminopropyl alkylglutamide, alkylaminopropionic acid, sodium alkylimidodipropionate and lauroamphocarboxyglycinate.
- acylamphohydroxypropylsulphonate, disodium acylamphodiacetate and sodium acylamphopropionate,
- N-alkylamino acids, for example aminopropyl alkylglutamide, alkylaminopropionic acid, sodium alkylimidodipropionate and lauroamphocarboxyglycinate.

D. Nonionic Surfactants

Nonionic surfactants which are advantageously used are
- alcohols,
- alkanolamides, such as cocamides MEA/DEA/MIPA,
- amine oxides, such as cocoamidopropylamine oxide,
- ethers, for example ethoxylated/propoxylated alcohols, ethoxylated/propoxylated esters, ethoxylated/propoxylated glycerol esters, ethoxylated/propoxylated cholesterols, ethoxylated/propoxylated triglyceride esters, ethoxylated/propoxylated lanolin, ethoxylated/propoxylated polysiloxanes, propoxylated POE ethers and alkyl polyglycosides, such as lauryl glucoside, decyl glucoside and coco-glycoside.
- sucrose esters, sucrose ethers
- polyglycerol esters, diglycerol esters, monoglycerol esters polyglyceryl-2 dipolyhydroxystearate (Dehymuls®PGPH), polyglyceryl-3 diisostearate (Lameform®TGI), polyglyceryl-4 isostearate (Isolan®GI 34), polyglyceryl-3 oleate, diisostearyl polyglyceryl-3 diisostearate (Isolan®PDI), polyglyceryl-3 methylglucose distearate (Tego Carey®450), polyglyceryl-3 beeswax (Cera Bellina®), polyglyceryl-4 caprate (polyglycerol caprate T2010/90), polyglyceryl-3 cetyl ether (Chimexane®NL), polyglyceryl-3 distearate (Cremophor®GS 32), polyglyceryl-2 stearate (Hostacerin®DGMS) and polyglyceryl polyricineoleate (Admul®WOL 1403), and mixtures thereof.

methylglucose esters, esters of hydroxy acids

The use of a combination of anionic and/or amphoteric surfactants with one or more nonionic surfactants is further advantageous.

In addition, cosmetic and dermatological preparations according to the present invention advantageously, but not obligatorily, comprise inorganic pigments based on finely disperse metal oxides and/or other metal compounds which are insoluble or sparingly soluble in water, in particular the oxides of titanium ($TiO_2$), zinc (ZnO), iron (e.g. $Fe_2O_3$), zirconium ($ZrO_2$), silicon ($SiO_2$), manganese (e.g. MnO), aluminum ($Al_2O_3$), cerium (e.g. $Ce_2O_3$), mixed oxides of the corresponding metals, and mixtures of such oxides. These pigments are X-ray-amorphous or non-X-ray-amorphous. More preference is given to pigments based on $TiO_2$. X-ray-amorphous oxide pigments are metal oxides or semi-metal oxides which reveal no or no recognizable crystalline structure in X-ray diffraction experiments. Such pigments are often obtainable by flame reaction, for example by reacting a metal or semi-metal halide with hydrogen and air (or pure oxygen) in a flame.

In cosmetic, dermatological or pharmaceutical formulations, X-ray-amorphous oxide pigments are used as thickeners and thixotropic agents, flow auxiliaries for emulsion and dispersion stabilisation and as carrier substance (for example for increasing the volume of finely divided powders). X-ray-amorphous oxide pigments which are known and often used in cosmetic or dermatological galenics are, for example, high-purity silicon oxide. Preference is given to high-purity, X-ray-amorphous silicon dioxide pigments with a particle size in the range from 5 to 40 nm and an active surface area (BET) in the range from 50 to 400 $m^2/g$, preferably 150 to 300 $m^2/g$, where the particles are to be regarded as spherical particles of very uniform dimension. Macroscopically, the silicon dioxide pigments are recognizable as loose, white powders. Silicon dioxide pigments are sold commercially under the name Aerosil® (CAS-No. 7631-85-9) or Carb-O-Sil Advantageous Aerosil® grades are, for example, Aerosil®OX50, Aerosil®130, Aerosil®150, Aerosil®200, Aerosil®300, Aerosil®380, Aerosil®MQX 80, Aerosil®MOX 170, Aerosil®COK 84, Aerosil®R 202, Aerosil®R 805, Aerosil®R 812, Aerosil®R 972, Aerosil®R 974, Aerosil®R 976.

According to the present invention, cosmetic or dermatological light protection preparations comprise 0.1 to 20% by weight, advantageously 0.5 to 10% by weight, more preferably 1 to 5% by weight, of X-ray-amorphous oxide pigments.

The non-X-ray-amorphous inorganic pigments are, according to the present invention, advantageously in hydrophobic form, i.e. have been surface-treated to repel water. This surface treatment may involve providing the pigments with a thin hydrophobic layer by processes known per se. Such a process involves, for example, producing the hydrophobic surface layer by a reaction according to

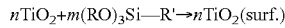

$nTiO_2 + m(RO)_3Si-R' \rightarrow nTiO_2(surf.)$ where n and m are stoichiometric parameters to be used as desired, and R and R' are the desired organic radicals. Hydrophobicised pigments prepared analogously to DE-A 33 14 742, for example, are advantageous.

For example, mention may be made of $TiO_2$ pigments, as are sold under the trade name T805 from Degussa. Preference is also given to $TiO_2/Fe_2O_3$ mixed oxides, as are supplied, for example, under the trade name T817, also from Degussa.

The total amount of inorganic pigments, in particular hydrophobic inorganic micropigments, in the finished cosmetic or dermatological preparations is advantageously chosen from the range from 0.1 to 30% by weight, preferably 0.1 to 10.0% by weight, preferably 0.5 to 6.0% by weight, based on the total weight of the preparations.

UV filters are commonly used in Cosmetic and dermatological formulations containing to prevent the skin from darkening and to lighten the skin. In this respect active skin lightening ingredients in addition to phenylbenzimidazole sulfonic acid neutralised with basic amino acids, either alone or in combination with other UV filters is preferred. Such skin lightening ingredients which can be used are for example but not limited to the following: kojic acid (5-hydroxy-2-hydroxymethyl-4-pyranone), kojic acid derivatives such as for example kojic dipalmitate, arbutin, ascorbic acid, ascorbic acid derivatives, hydroquinone, hydroquinone derivatives, styryl resorcinol derivatives (e.g. 4-(1-phenylethyl)1,3-benzenediol), molecules containing sulphur, such as glutathione or cysteine for example, alpha-hydroxy acids (e.g. citric acid, lactic acid, malic acid) and their derivatives, N-acetyltyrosine and derivatives, undecenoylphenylalanine, gluconic acid, chromone derivatives such as aloesin, flavonoids, thymol derivatives, 1-aminoethylphosphinic acid, thiourea derivatives, ellagic acid, nicotinamide, zinc salts such as zinc chloride or zinc gluconate for example, thujaplicine and derivatives, triterpenes such as maslic acid, sterols such as ergosterol, benzofuranones such as senkyunolide, vinyl- and ethylguaiacol, dionic acids such as octodecenedionic acid and azelaic acid, nitrogen oxide synthesis inhibitors such as L-nitroarginine and its derivatives, 2,7-dinitroindazole or thiocitrulline, metal chelators (e.g. alpha-hydroxy fatty acids, palmitic acid, phytic acid, lactoferrin, humic acid, gallic acid, bile extracts, bilirubin, biliverdin), retinoids, soja milk, soya extract, serine protease inhibitors or lipoic acid or other synthetic or natural active compounds for skin and hair lightening, these compounds also being used in the form of an extract from plants, such as bearberry extract, rice extract, papaya extract, liquorice root extract or constituents concentrated from these, such as glabridin or licochalcone A, Artocarpus extract, extract from Rumex and Ramulus species, extracts from pine species (Pinus) and extracts from Vitis species or stilbene derivatives concentrated from these, extract from saxifraga, mulberry, Scutelleria and/or grapes.

An additional content of antioxidants in the cosmetic or dermatological preparation is generally preferred. According to the present invention, favorable antioxidants which can be used are all antioxidants customary or suitable for cosmetic and/or dermatological applications.

The antioxidants are advantageously chosen from the group of amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. α-carotene, β-carotene, lycopene) and derivatives thereof, chlorogenic acid and derivatives thereof, lipoic acid and derivatives thereof (e.g. dihydrolipoic acid), aurothioglucose, propylthiouracil and other thiols (e.g. thioredoxin, glutathione, cysteine, cystine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (e.g. buthionine sulfoximines, homocysteine sulfoximine, buthionine sulfones, penta-, hexa-, heptathionine sulfoximine) in very low tolerated doses (e.g. pmol to µmol/kg), and also (metal) chelating agents (e.g. α-hydroxy fatty acids, palmitic acid, phytic acid, lactoferrin), α-hydroxy acids (e.g. citric acid, lactic acid, maleic acid), humic acid, bile acid, bile extracts, biliverdin, EDTA, EGTA and derivatives thereof, unsaturated fatty acids and derivatives thereof (e.g. γ-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives (e.g. vitamin E acetate), vitamin A and derivatives (vitamin A palmitate), and coniferyl benzoate of benzoin resin, rutinic acid and derivatives thereof, α-glycosylrutin, ferulic acid, furfurylideneglucitol, carnosine, butylhydroxytoluene, butylhydroxyanisol, nordihydroguaiacic acid, nordihydroguaiaretic acid, trihydroxybutyrophenone, uric acid and derivatives thereof, mannose and derivatives thereof, zinc and derivatives thereof (e.g. ZnO, $ZnSO_4$), selenium and derivatives thereof (e.g. selenomethionine), stilbenes and derivatives thereof (e.g. stilbene oxide, trans-stilbene oxide) and the derivatives (salts, esters, ethers, sugars, nucleotides, nucleosides, peptides and lipids) of the active ingredients suitable according to the present invention.

The amount of the above-mentioned antioxidants (one or more compounds) in the preparations is preferably 0.001 to 30% by weight, more preferably 0.05 to 20% by weight, and most preferably 1 to 10% by weight, based on the total weight of the preparation.

Preferred embodiments of the cosmetic and/or pharmaceutical, especially dermatologically active preparations of the invention may advantageously also comprise vitamins and vitamin precursors, it being possible for all the vitamins and vitamin precursors which are suitable or usual for cosmetic and/or dermatological applications to be used. Those worth mentioning here are, in particular, vitamins and vitamin precursors, such as tocopherols, vitamin A, niacin acid and niacinamide, further vitamins of the B complex, in particular biotin, and vitamin C and panthenol and derivatives thereof, in particular the esters and ethers of panthenol, and cationically derivatised panthenols, such as panthenol triacetate, panthenol monoethyl ether and the monoacetate thereof and cationic panthenol derivatives. If vitamin E and/or derivatives thereof represent the antioxidant(s), it is advantageous to choose their respective concentrations from the range from 0.001 to 10% by weight, based on the total weight of the formulation. If vitamin A or vitamin A derivatives, or carotenes or derivatives thereof represent the antioxidant(s), it is advantageous to choose their respective concentrations from the range from 0.001 to 10% by weight, based on the total weight of the formulation.

Preferred embodiments of the cosmetic and/or pharmaceutical, especially dermatological preparations of the invention may also comprise lipids chosen from the following group of substances:
(i) linear or branched saturated paraffins (mineral oils) having 15 or more C atoms, in particular having 18 to 45 C atoms;
(ii) esters having 12 or more C atoms of linear or branched fatty acids having 6 to 30 C atoms and linear or branched, saturated or unsaturated mono-, di- or triols having 3 to 30 C atoms, these esters having no free hydroxyl groups;
(iii) esters of benzoic acid and linear or branched, saturated or unsaturated monoalkanols having 8 to 20 C atoms;
(iv) monoesters or diesters of alcohols having 3 to 30 C atoms and naphthalene-monocarboxylic or -dicarboxylic acids; especially naphthalenemonocarboxylic acid $C_6$-$C_{18}$ esters and naphthalenedicarboxylic acid di-$C_6$-$C_{18}$ esters;
(v) linear or branched, saturated or unsaturated di-$C_6$-$C_{18}$-alkyl ethers;
(vi) silicone oils;
(vii) 2-alkyl-1-alkanols of the formula (III)

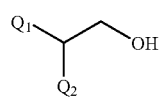

(III)

where
$Q_1$ is a linear or branched alkyl radical having 6 to 24 C atoms and
$Q_2$ is a linear or branched alkyl radical having 4 to 16 C atoms.

An oil phase or oil component in the narrower (and preferred) sense of the present invention, i.e. of the inventively limited substances or substances present only in a minor fraction, encompasses the following groups of substances:
(i) linear or branched, saturated paraffins having 20 to 32 C atoms;
(ii) esters having at least 14 C atoms of linear or branched, saturated fatty acids having 8 to 24 C atoms and linear or branched, saturated or unsaturated mono-, di- or triols having 3 to 24 C atoms, these esters containing no free hydroxyl groups;
(iii) esters of benzoic acid and linear or branched, saturated monoalkanols having 10 to 18 C atoms;
(iv) 2,6-naphthalenedicarboxylic acid di-C6-C12 esters;
(v) linear or branched, saturated di-C6-C18-alkyl ethers, especially (straight-chain) di-C6-C12-alkyl ethers;
(vi) silicone oils from the group of the cyclotrisiloxanes, cyclopentasiloxanes, dimethylpolysiloxanes, diethylpolysiloxanes, methylphenylpolysiloxanes, diphenylpolysiloxanes and hybrid forms thereof;
(vii) 2-alkyl-1-alkanols having 12 to 32 C atoms of the formula (III)
where
$Q_1$ is a (preferably linear) alkyl radical having 6 to 18 C atoms and
$Q_2$ is a (preferably linear) alkyl radical having 4 to 16 C atoms.

An oil phase in the narrowest (and most preferred) sense of the present invention encompasses the following groups of substances:
(i) linear or branched, saturated paraffins having 20 to 32 C atoms such as isoeicosane or squalane;
(ii) esters having at least 16 C atoms of linear or branched, saturated fatty acids having 8 to 18 C atoms and linear or branched, saturated mono-, di- or triols having 3 to 18 C atoms, these esters containing no free hydroxyl groups;
(iii) esters of benzoic acid and linear or branched, saturated monoalkanols having 12 to 15 C atoms, especially $C_{12\text{-}15}$-alkyl benzoates;
(iv) 2,6-naphthalenedicarboxylic acid di-C6-C10 esters, especially diethylhexyl 2,6-naphthalenedicarboxylate;
(v) straight-chain di-$C_6$-$C_{10}$-alkyl ethers; especially di-n-octyl ether (dicaprylyl ether);

(vi) silicone oils from the group undecamethylcyclotrisiloxane, cyclomethicone, decamethylcyclopentasiloxane, dimethylpolysiloxanes, diethylpolysiloxanes, methylphenylpolysiloxanes and diphenylpolysiloxanes;

(vii) 2-alkyl-1-alkanols having 12 to 32 C atoms of the formula (III)

where $Q_1$ is a (preferably linear) alkyl radical having 6 to 18 C atoms and $Q_2$ is a (preferably linear) alkyl radical having 4 to 16 C atoms.

Particularly preferred components of type (i) in the oil phase are as follows: isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate, 2-ethylhexyl isostearate, isotridecyl isononanoate, 2-ethylhexyl cocoate, caprylic/capric triglyceride, and also synthetic, semisynthetic and natural mixtures of such esters, e.g. jojoba oil.

Fatty acid triglycerides (oil components of type (i) in the oil phase) may also be in the form of, or in the form of a constituent of, synthetic, semisynthetic and/or natural oils, examples being olive oil, sunflower oil, soya oil, peanut oil, rapeseed oil, almond oil, palm oil, coconut oil, palm kernel oil and mixtures thereof.

Particularly preferred oil components of type (vii) in the oil phase are as follows: 2-butyl-1-octanol, 2-hexyl-1-decanol, 2-octyl-1-dodecanol, 2-decyltetradecanol, 2-dodecyl-1-hexadecanol and 2-tetradecyl-1-octadecanol.

Particularly preferred oil components in the oil phase are mixtures comprising $C_{12}$-$C_{15}$-alkyl benzoate and 2-ethylhexyl isostearate, mixtures comprising $C_{12}$-$C_{15}$-alkyl benzoate and isotridecyl isononanoate, mixtures comprising $C_{12}$-$C_{15}$-alkyl benzoate, 2-ethylhexyl isostearate and isotridecyl isononanoate, mixtures comprising cyclomethicone and isotridecyl isononanoate, and mixtures comprising cyclomethicone and 2-ethylhexyl isostearate.

Preferred embodiments of the cosmetic and/or pharmaceutical, especially dermatologically active preparations of the invention may advantageously also comprise the use of polymers to improve the spreadability of the formulation upon the skin or hair, or improve the water and or sweat and or rub-off resistancy of the formula and to improve the protection factor of the formulation. Examples of such polymers are: VP/Eicosene copolymers sold under the trade name of Antaron V-220 by International Speciality Products, VP/Hexadecene copolymer sold under the trade names Antaron V-216 and Antaron V-516 by International Speciality Products, Tricontanyl PVP sold under the trade name of Antaron WP-660 by International Speciality Products, Isohexadecane and Ethylene/Propylene/Styrene copolymer and Butylene/Styrene copolymer sold under the trade names of Versagel MC and MD by Penreco, Hydrogenated polyisobutene and Ethylene/Propylene/Styrene copolymer and Butylene/Styrene copolymer sold under the trade mane of Versagel ME by Penreco, Acrylates/Octylacrylamide Copolymers sold under the trade name of Dermacryl 79, Dermacryl AQF and Dermacryl LT by National Starch, Polyurethanes such as PPG-17/IPDI/DMPA copolymer sold under the trade name of Avalure UR 450 & 525 sold by Noveon, Polyurethanes-2 and -4 sold under the trade names Avalure UR-405, -410, -425, -430 and -445 525 sold by Noveon, Polyurethane 5 and Butyl Acetate and isopropyl alcohol sold under the trade name Avalure UR-510 and -525 sold by Noveon, Polyurethanes-1 and -6 sold under the trade name of Luviset PUR by BASF, Hydrogenated Dimer Dilinoleyl/Dimethylcarbonate Copolymer sold under the trade name of Cosmedia DC by Cognis.

Of course, as one well versed in the art of cosmetic and dermatological formulation knows, this is not an exhaustive list and other suitable polymers not listed here may be used. Examples of such polymers may be found in the latest edition of the CTFA's International Cosmetic Ingredient Dictionary The amount of polymers used to obtain the desired effect in the formulation range from 0.10% to 5.0% by weight of the formulation and especially in the range from 0.25% to 3.0% by weight of the formulation.

Preferred embodiments of the cosmetic and/or pharmaceutical, especially dermatologically active preparations of the invention comprise, if desired, further ingredients having care properties, such as, for example, fatty alcohols having 6 to 30 C atoms. The fatty alcohols here can be saturated or unsaturated and linear or branched. Furthermore, these fatty alcohols can in some cases be part of the oil phase (III) if they correspond to the definition given there. Alcohols which can be employed are, for example, decanol, decenol, octanol, octenol, dodecanol, dodecenol, octadienol, decadienol, dodecadienol, oleyl alcohol, ricinoleyl alcohol, erucyl alcohol, stearyl alcohol, isostearyl alcohol, cetyl alcohol, lauryl alcohol, myristyl alcohol, arachidyl alcohol, caprylyl alcohol, capryl alcohol, linoleyl alcohol, linolenyl alcohol and behenyl alcohol, and also Guerbet alcohols thereof, such as, for example, 2-octyl-1-dodecanol, it being possible for the list to be extended virtually as desired by further alcohols of related structural chemistry. The fatty alcohols preferably originate from natural fatty acids, being conventionally prepared from the corresponding esters of the fatty acids by reduction. Fatty alcohol fractions which are formed by reduction from naturally occurring fats and fatty oils, such as beef tallow, peanut oil, colza oil, cottonseed oil, soya oil, sunflower oil, palm kernel oil, linseed oil, maize oil, castor oil, rapeseed oil, sesame oil, cacao butter and coconut fat, can further be employed.

Substances having care properties which can be employed in an outstanding manner in the cosmetic and/or dermatologically active preparations stabilised by means of the methods of the invention and comprising phenolic compounds of the formula (I), further include ceramides, where ceramides are understood as meaning N-acylsphingosins (fatty acid amides of sphingosin) or synthetic analogues of such lipids (so-called pseudoceramides), which significantly improve the water retention capacity of the stratum corneum.

phospholipids, for example soya lecithin, egg lecithin and cephalins fatty acids phytosterols and phytosterol-containing fats or waxes vaseline, paraffin oils and silicone oils; the latter include, inter alia, dialkyl- and alkylarylsiloxanes, such as dimethylpolysiloxane and methylphenylpolysiloxane, and also alkoxylated and quaternised derivatives thereof.

Animal and/or plant protein hydrolysates can advantageously also be added to preferred embodiments of cosmetic and/or pharmaceutical, especially dermatologically active, preparations of the invention. Substances which are advantageous in this respect are, in particular, elastin, collagen, keratin, milk protein, soya protein, oat protein, pea protein, almond protein and wheat protein fractions or corresponding protein hydrolysates, and also condensation products thereof with fatty acids, and quaternised protein hydrolysates, the use of plant protein hydrolysates being preferred.

The aqueous phase of the preparations according to the present invention optionally advantageously comprises alcohols, diols or polyols (lower alkyl), and ethers thereof, preferably ethanol, isopropanol, propylene glycol, 1,2-hexanediol, 1,2-octanediol, 1,2-decanediol, a mixture of 1,2-hexanediol and 1,2-octanediol, a mixture of 1,2-hexanediol and 1,2-decanediol, a mixture of 1,2-octanediol and 1,2-decanediol, a mixture of 1,2-hexanediol, 1,2-octanediol and 1,2-decanediol, glycerol, ethylene glycol-monoethyl or monobutyl ether, propylene glycol monomethyl, -monoethyl or monobutyl ether, diethylene glycol monomethyl or -monoethyl ether and analogous products, and also alcohols (lower alkyl), e.g. ethanol, 1,2-propanediol, glycerol, and, in particular, one or more thickeners which can advantageously be chosen from the group of silicon dioxide, aluminum silicates, polysaccharides and derivatives thereof, e.g. hyaluronic acid, xanthan gum, hydroxypropylmethylcellulose, particularly advantageously from the group of polyacrylates, preferably a polyacrylate from the group of so-called Carbopols, for example, Carbopol grades 980, 981, 1382, 2984, 5984, in each case individually or in combination.

Preferred embodiments of the cosmetic and/or pharmaceutical, especially dermatologically active preparations of the invention may also comprise active anti-inflammatory and/or redness- and/or itching-alleviating compounds (anti-irritants). All the active anti-inflammatory or redness- and/or itching-alleviating compounds which are suitable or usual for cosmetic and/or dermatological applications can be used here. Active anti-inflammatory and redness- and/or itching-alleviating compounds which are advantageously employed are steroidal anti-inflammatory substances of the corticosteroid type, such as hydrocortisone, dexamethasone, dexamethasone phosphate, methylprednisolone or cortisone, it being possible for the list to be extended by addition of further steroidal anti-inflammatories. Non-steroidal anti-inflammatories can also be employed. Those to be mentioned here by way of example are oxicams, such as piroxicam or tenoxicam; salicylates, such as aspirin, Disalcid, Solprin or fendosal; acetic acid derivatives, such as diclofenac, fenclofenac, indomethacin, sulindac, tolmetin, or clindanac; fenamates, such as mefenamic, meclofenamic, flufenamic or niflumic; propionic acid derivatives, such as ibuprofen, naproxen, benoxaprofen or pyrazoles, such as phenylbutazone, oxyphenylbutazone, febrazone or azapropazone.

Alternatively, natural anti-inflammatory or redness- and/or itching-alleviating substances can be employed. Plant extracts, specific highly active plant extract fractions and highly pure active substances isolated from plant extracts can be employed. Extracts, fractions and active substances from camomile, aloe vera, Commiphora species, Rubia species, willow, rose-bay willow-herb, oats, and also pure substances, such as, inter alia, bisabolol, apigenin 7-glucoside, boswellic acid, phytosterols, glycyrrhizic acid, glabridin or licochalcone A, are particularly preferred. The preparations comprising phenylbenzimidazole sulfonic acid neutralised with basic amino acids can also comprise mixtures of two or more active anti-inflammatory compounds. Bisabolol, boswellic acid, and also extracts and isolated highly pure active compounds from oats and Echinacea are particularly preferred for use in the context of the invention as anti-inflammatory and redness- and/or itching-alleviating substances, and alpha-bisabolol and extracts and isolated highly pure active compounds from oats are especially preferred.

The amount of anti-irritants (one or more compounds) in the preparations is preferably 0.0001% to 20% by weight, with particular preference 0.0001% to 10% by weight, in particular 0.001% to 5% by weight, based on the total weight of the preparation.

Preferred embodiments of the cosmetic and/or pharmaceutical, especially dermatologically active preparations of the invention may advantageously also comprise moisture retention regulators. The following substances for example are used as moisture retention regulators (moisturizers): sodium lactate, urea, alcohols, sorbitol, glycerol, propylene glycol, aliphatic 1,2-diols with a C number of 5-10, collagen, elastin or hyaluronic acid, diacyl adipates, petrolatum, ectoin, urocanic acid, lecithin, panthenol, phytantriol, lycopene, algae extract, ceramides, cholesterol, glycolipids, chitosan, chondroitin sulphate, polyamino acids and polyamino sugars, lanolin, lanolin esters, amino acids, alpha-hydroxy acids (e.g. citric acid, lactic acid, malic acid) and derivatives thereof, sugars (e.g. inositol), alpha-hydroxy fatty acids, phytosterols, triterpene acids, such as betulinic acid or ursolic acid, algae extracts.

Preferred embodiments of the cosmetic and/or pharmaceutical, especially dermatologically active preparations of the invention may advantageously also comprise mono-, di- and oligosaccharides, such as, for example, glucose, galactose, fructose, mannose, fruit sugars and lactose.

Preferred embodiments of the cosmetic and/or pharmaceutical, especially dermatologically active preparations of the invention may advantageously also comprise plant extracts, which are conventionally prepared by extraction of the whole plant, but also in individual cases exclusively from blossom and/or leaves, wood, bark or roots of the plant. In respect of the plant extracts which can be used, reference is made in particular to the extracts which are listed in the table starting on page 44 of the 3rd edition of the Leitfaden zur Inhaltsstoffdeklaration kosmetischer Mittel [Manual of Declaration of the Constituents of Cosmetic Compositions], published by Industrieverband Körperpflegemittel and Waschmittel e.V. (IKW), Frankfurt. Extracts which are advantageous in particular are those from aloe, witch hazel, algae, oak bark, rose-bay willow-herb, stinging nettle, dead nettle, hops, camomile, yarrow, arnica, calendula, burdock root, horsetail, hawthorn, linden blossom, almond, pine needle, horse chestnut, sandalwood, juniper, coconut, mango, apricot, orange, lemon, lime, grapefruit, apple, green tea, grapefruit pip, wheat, oats, barley, sage, thyme, wild thyme, rosemary, birch, mallow, lady's smock, willow bark, restharrow, coltsfoot, hibiscus, ginseng and ginger root.

In this context, the extracts from aloe vera, camomile, algae, rosemary, calendula, ginseng, cucumber, sage, stinging nettle, linden blossom, arnica and witch hazel are particularly preferred. Mixtures of two or more plant extracts can also be employed. Extraction agents which can be used for the preparation of plant extracts mentioned are, inter alia, water, alcohols and mixtures thereof. In this context, among the alcohols lower alcohols, such as ethanol and isopropanol, but also polyhydric alcohols, such as ethylene glycol, propylene glycol and butylene glycol, are preferred, and in particular both as the sole extraction agent and in mixtures with water. The plant extracts can be employed both in pure and in diluted form.

Preferred embodiments of the cosmetic and/or pharmaceutical, especially dermatologically active preparations of the invention may in numerous cases advantageously comprise the following preservatives:

Preservatives which are preferably chosen here are those such as benzoic acid, its esters and salts, propionic acid and its salts, salicylic acid and its salts, 2,4-hexadienoic acid (sorbic acid) and its salts, formaldehyde and paraformaldehyde, 2-hydroxybiphenyl ether and its salts, 2-zincsulphidopyridine N-oxide, inorganic sulphites and bisulphites, sodium iodate, chlorobutanolum, 4-ethylmercuryl(II)-5-amino-1,3-bis(2-hydroxybenzoic acid), its salts and esters, dehydracetic acid, formic acid, 1,6-bis(4-amidino-2-bromophenoxy)-n-hexane and its salts, the sodium salt of ethylmercury(II)-thiosalicylic acid, phenylmercury and its salts, 10-undecylenic acid and its salts, 5-amino-1,3-bis(2-ethylhexyl)-5-methyl-hexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)urea, 4-chloro-m-cresol, 2,4,4'-trichloro-2'-hydroxydiphenyl ether, 4-chloro-3,5-dimethylphenol, 1,1'-methylene-bis(3-(1-hydroxymethyl-2,4-dioxoimidazolidin-5-yl)urea), poly (hexamethylene diguanide) hydrochloride, 2-phenoxyethanol, hexamethylenetetramine, 1-(3-chloroallyl)-3,5,7-triaza-1-azoniaadamantane chloride, 1-(4-chlorophenoxy)-1-(1H-imidazol-1-yl)-3,3-dimethyl-2-butanone, 1,3-bis-(hydroxymethyl)-5,5-dimethyl-2,4-imidazolidinedione, benzyl alcohol, octopirox, 1,2-dibromo-2,4-dicyanobutane, 2,2'-methylenebis(6-bromo-4-chlorophenol), bromochlorophene, mixture of 5-chloro-2-methyl-3(2H)-isothiazolinone and 2-methyl-3(2H)isothiazolinone with magnesium chloride and magnesium nitrate, 2-benzyl-4-chlorophenol, 2-chloroacetamide, chlorhexidine, chlorhexidine acetate, chlorhexidine gluconate, chlorhexidine hydrochloride, 1-phenoxypropan-2-ol, N-alkyl($C_{12}$-$C_{22}$)trimethylammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxymethylurea, 1,6-bis(4-amidinophenoxy)-n-hexane and its salts, glutaraldehyde, 5-ethyl-1-aza-3,7-dioxabicyclo[3.3.0]octane, 3-(4-chlorophenoxy)-1,2-propanediol, hyamines, alkyl-($C_8$-$C_{18}$)-dimethylbenzylammonium chloride, alkyl-($C_8$-$C_{18}$)-dimethylbenzylammonium bromide, alkyl-($C_8$-$C_{18}$)-dimethylbenzylammonium saccharinate, benzyl hemiformal, 3-iodo-2-propynyl butylcarbamate, sodium hydroxymethylaminoacetate or sodium hydroxymethylaminoacetate.

In various cases it may also be advantageous to employ substances which are chiefly employed for inhibition of the growth of undesirable microorganisms on or in animal organisms in cosmetic and/or pharmaceutical, especially dermatologically active, preparations of the invention. In this respect, in addition to conventional preservatives, further active compounds which are worth mentioning, in addition to the large group of conventional antibiotics, are, in particular, the products relevant for cosmetics, such as triclosan, climbazol, octoxyglycerol, octopirox (1-hydroxy-4-methyl-6-(2,4,4-trimethylpentyl)-2(1H)-pyridone, 2-aminoethanol), chitosan, farnesol, glycerol monolaurate or combinations of the substances mentioned, which are employed, inter alia, against underarm odour, foot odour or dandruff formation.

Furthermore, cosmetic and/or pharmaceutical, especially dermatologically active preparations of the invention may also comprise substances having a cooling action. Individual active cooling compounds which are preferred for use in the context of the present invention are listed below. The skilled person is able to supplement the following list with a large number of further active cooling compounds; the active cooling compounds listed can also be employed in combination with one another: l-menthol, d-menthol, racemic menthol, menthone glycerol acetal (trade name: Frescolat®MGA), menthyl lactate (trade name: Frescolat®ML, menthyl lactate is preferably l-menthyl lactate, in particular l-menthyl l-lactate), substituted menthyl-3-carboxylic acid amides (e.g. menthyl-3-carboxylic acid N-ethylamide), 2-isopropyl-N-2,3-trimethylbutanamide, substituted cyclohexanecarboxylic acid amides, 3-menthoxypropane-1,2-diol, 2-hydroxyethyl menthyl carbonate, 2-hydroxypropyl menthyl carbonate, N-acetylglycine menthyl ester, isopulegol, menthyl hydroxycarboxylic acid esters (e.g. menthyl 3-hydroxybutyrate), monomenthyl succinate, 2-mercaptocyclodecanone, menthyl 2-pyrrolidin-5-onecarboxylate, 2,3-dihydroxy-p-menthane, 3,3,5-trimethylcyclohexanone glycerol ketal, 3-menthyl 3,6-di- and -trioxaalkanoates, 3-menthyl methoxyacetate, icilin.

Preferred active cooling compounds are: l-menthol, d-menthol, racemic menthol, menthone glycerol acetal (trade name: Frescolat®MGA), menthyl lactate (preferably l-menthyl lactate, in particular l-menthyl l-lactate, trade name: Frescolat®ML), substituted menthyl-3-carboxylic acid amides (e.g. menthyl-3-carboxylic acid N-ethylamide), 2-isopropyl-N-2,3-trimethylbutanamide, substituted cyclohexanecarboxylic acid amides, 3-menthoxypropane-1,2-diol, 2-hydroxyethyl menthyl carbonate, 2-hydroxypropyl menthyl carbonate, isopulegol.

Particularly preferred active cooling compounds are: l-menthol, racemic menthol, menthone glycerol acetal (trade name: Frescolat®MGA), menthyl lactate (preferably l-menthyl lactate, in particular l-menthyl l-lactate, trade name: Frescolat®ML), 3-menthoxypropane-1,2-diol, 2-hydroxyethyl menthyl carbonate, 2-hydroxypropyl menthyl carbonate.

Very particularly preferred active cooling compounds are: l-menthol, menthone glycerol acetal (trade name: Frescolat®MGA), menthyl lactate (preferably l-menthyl lactate, in particular l-menthyl l-lactate, trade name: Frescolat®ML).

The use concentration of the active cooling compounds to be employed is, depending on the substance, preferably in the concentration range from 0.01% to 20% by weight, and more preferably in the concentration range from 0.1% to 5% by weight, based on the total weight of the completed (ready-to-use) cosmetic or pharmaceutical preparation.

The invention is further described by the accompanying figures and examples, without limiting the scope of the claims.

Figure 2:
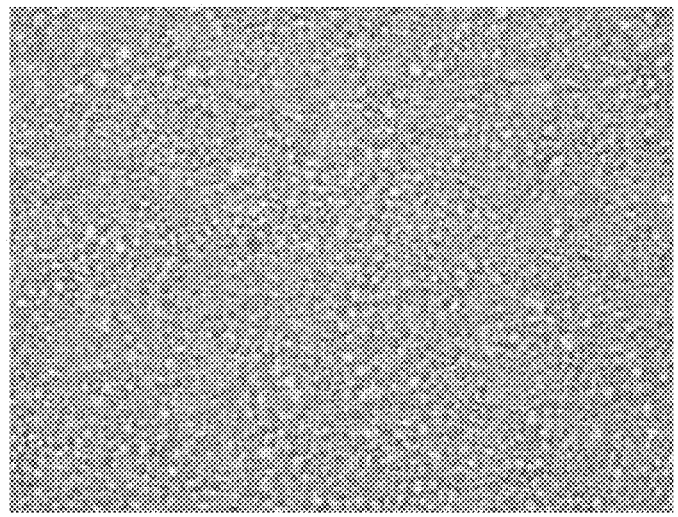
Figure 3:
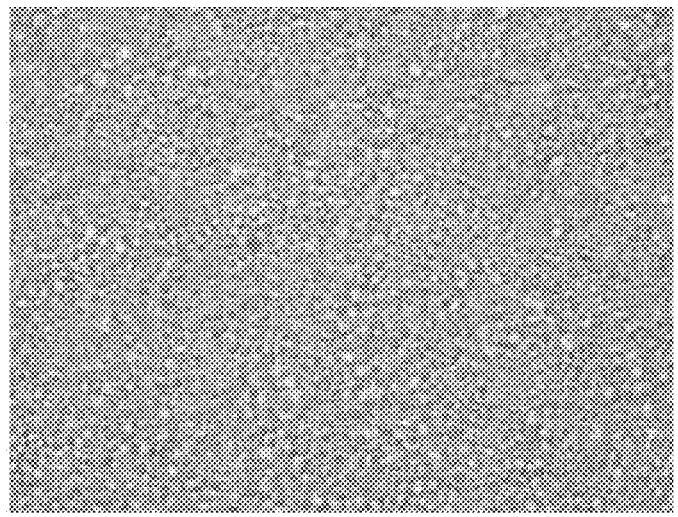
Figure 4:
Figure 5:
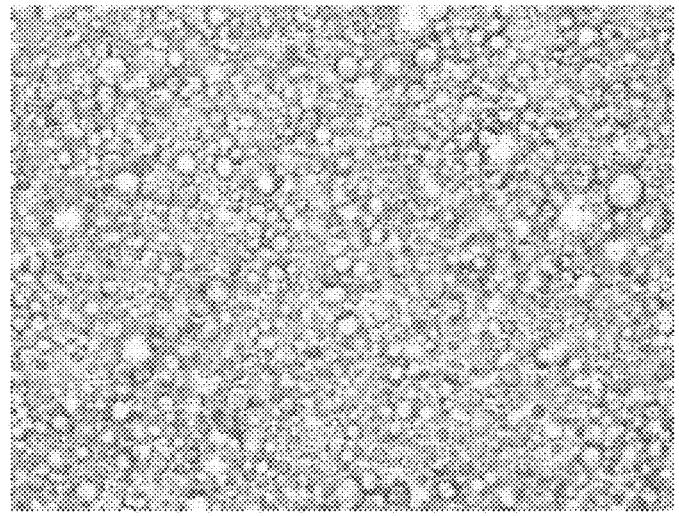
Figure 6:
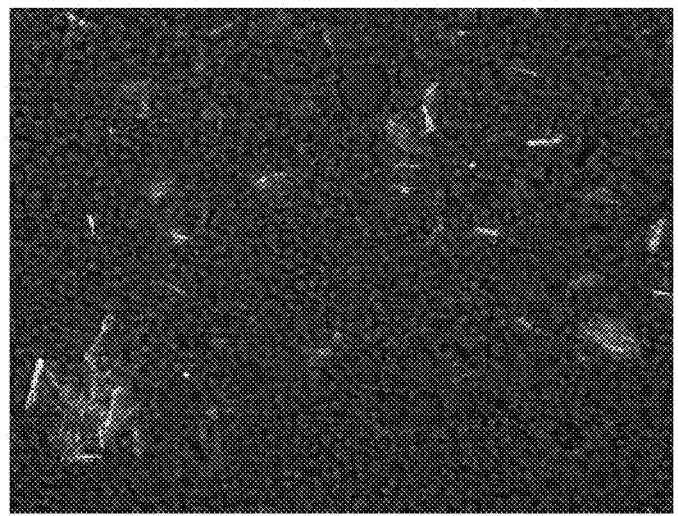
Figure 7:
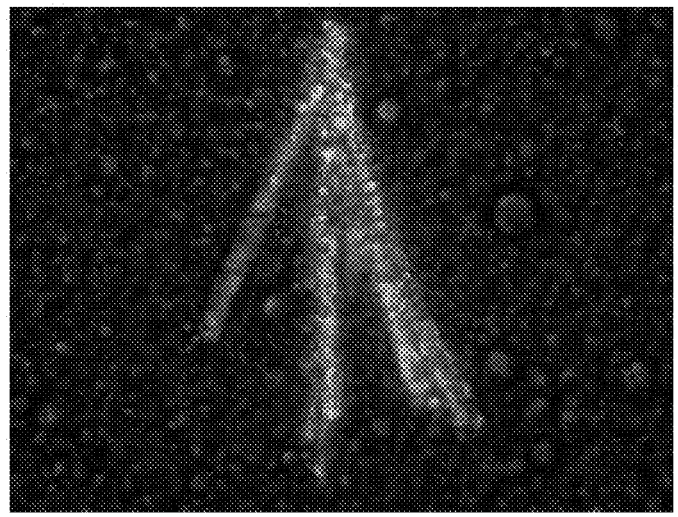

FIG. 1: A microphotograph of an oil in water emulsion at pH 6.9 containing phenylbenzimidazole sulfonic acid neutralised with sodium hydroxide, crystals of phenylbenzimidazole sulfonic acid being clearly visible;

FIG. 2: a microphotograph of oil in water emulsion example 1c, formulation A (neutralised with Arginine to pH 7.0);

FIG. 3: a microphotograph of an oil in water emulsion example 1c, formulation B (neutralised with Triethanolamine to pH 7.0);

FIG. 4: a microphotograph of an oil in water emulsion example 1c, formulation C (neutralised with Sodium Hydroxide to pH 7.0);

FIG. 5: a microphotograph of oil in water emulsion example 1a, formulation A (neutralised with Arginine to pH 6.0) showing that no crystallisation of phenylbenzimidazole sulfonic acid occurs;

FIG. 6: a microphotograph of oil in water emulsion example 1a, formulation B (neutralised with Triethanolamine to pH 6.0), showing crystals of phenylbenzimidazole sulfonic acid; and FIG. 7: a microphotograph of an oil in water emulsion example 1a, formulation B (neutralised with Sodium Hydroxide to pH 6.0), showing crystals of phenylbenzimidazole sulfonic acid.

EXAMPLES

Commercially available 2-Phenylbenzimidazole-5-sulfonic acid was used [Neo Heliopan® Hydro, from Symrise GmbH & Co. KG, Holzminden, Germany]. Unless stated otherwise, the data relate to the weight.

Crystallisation.

By way of example, comparative observations between formulations containing phenylbenzimidazole sulfonic acid neutralised with basic amino acids with formulations containing phenylbenzimidazole sulfonic acid neutralised with traditional amines or hard bases are listed below:

Example 1a

|   | Ingredient: | INCI | A wt.-% | B wt.-% | C wt.-% |
|---|---|---|---|---|---|
| A | Emulgade SE PF | Glycerylstearate, cetearylalcohol, cetyl Palmitate | 6.00 | 6.00 | 6.00 |
|   | Lanette O | Cetearylalcohol | 1.50 | 1.50 | 1.50 |
|   | Cetiol V | Decyl Oleate | 4.00 | 4.00 | 4.00 |
|   | Cetiol 868 | Ethylhexyl stearate | 8.00 | 8.00 | 8.00 |
|   | Shea Butter | *Butyrospermum parkii* | 3.00 | 3.00 | 3.00 |
| B | Water | Aqua | Ad 100 | Ad 100 | Ad 100 |
|   | 1,2-Propylene glycol | Propylene glycol | 2.64 | 2.64 | 2.64 |
|   | Germaben 2 | Propylene glycol, diazolidenyl urea Methyl paraben, propyl paraben | 0.44 | 0.44 | 0.44 |
|   | Neo Heliopan Hydro | Phenylbenzimidazole sulfonic acid | 3.30 | 3.30 | 3.30 |
|   | Arginine |  | 2.00 | 0.0 | 0.0 |
|   | Triethanolamine |  | 0.0 | 1.60 | 0.0 |
|   | Sodium Hydroxide |  | 0.0 | 0.0 | 4.50 |
|   | pH after manufacturing |  | 6.0 | 6.0 | 6.0 |

Example 1b

|   | Ingredient: | INCI | A wt.-% | B wt.-% | C wt.-% |
|---|---|---|---|---|---|
| A | Emulgade SE PF | Glycerylstearate, cetearylalcohol, cetyl Palmitate | 6.00 | 6.00 | 6.00 |
|   | Lanette O | Cetearylalcohol | 1.50 | 1.50 | 1.50 |
|   | Cetiol V | Decyl Oleate | 4.00 | 4.00 | 4.00 |
|   | Cetiol 868 | Ethylhexyl stearate | 8.00 | 8.00 | 8.00 |
|   | Shea Butter | *Butyrospermum parkii* | 3.00 | 3.00 | 3.00 |
| B | Water | Aqua | Ad 100 | Ad 100 | Ad 100 |
|   | 1,2-Propylene glycol | Propylene glycol | 2.64 | 2.64 | 2.64 |
|   | Germaben 2 | Propylene glycol, diazolidenyl urea Methyl paraben, propyl paraben | 0.44 | 0.44 | 0.44 |
|   | Neo Heliopan Hydro | Phenylbenzimidazole sulfonic acid | 3.30 | 3.30 | 3.30 |
|   | Arginine |  | 2.05 | 0.0 | 0.0 |
|   | Triethanolamine |  | 0.0 | 1.70 | 0.0 |
|   | Sodium Hydroxide |  | 0.0 | 0.0 | 4.65 |
|   | pH after manufacturing |  | 6.5 | 6.5 | 6.5 |

Example 1c

|   | Ingredient: | INCI | A wt.-% | B wt.-% | C wt.-% |
|---|---|---|---|---|---|
| A | Emulgade SE PF | Glycerylstearate, cetearylalcohol, cetyl Palmitate | 6.00 | 6.00 | 6.00 |
|   | Lanette O | Cetearylalcohol | 1.50 | 1.50 | 1.50 |
|   | Cetiol V | Decyl Oleate | 4.00 | 4.00 | 4.00 |
|   | Cetiol 868 | Ethylhexyl stearate | 8.00 | 8.00 | 8.00 |
|   | Shea Butter | *Butyrospermum parkii* | 3.00 | 3.00 | 3.00 |
| B | Water | Aqua | Ad 100 | Ad 100 | Ad 100 |
|   | 1,2-Propylene glycol | Propylene glycol | 2.64 | 2.64 | 2.64 |
|   | Germaben 2 | Propylene glycol, diazolidenyl urea Methyl paraben, propyl paraben | 0.44 | 0.44 | 0.44 |
|   | Neo Heliopan Hydro | Phenylbenzimidazole sulfonic acid | 3.30 | 3.30 | 3.30 |
|   | Arginine |  | 2.10 | 0.0 | 0.0 |
|   | Triethanolamine |  | 0.0 | 2.00 | 0.0 |
|   | Sodium Hydroxide |  | 0.0 | 0.0 | 4.75 |
|   | pH after manufacturing |  | 7.0 | 7.0 | 7.0 |

Manufacturing Procedure.

Ingredients of phase A were mixed and heated with stirring at 80° C. The ingredients of phase A were mixed together and heated at 80° C. with vigorous stirring until all of the phenylbenzimidazole sulfonic acid had been neutralised and dissolved into solution. Phases A & B were then mixed together with stirring and allowed to cool to room temperature and put into storage test.

Results. No crystallisation of Phenylbenzimidazole sulfonic acid was observed after manufacture of emulsions 1c-A, B & C after 1 month storage at 5° C. and ambient temperature (22° C.) (see FIGS. 2-7).

Crystallisation of phenylbenzimidazole sulfonic acid was seen in all other emulsions except for 1a-A and 1b-A after the same time period.

Example 2a

| | Ingredient | INCI | A wt.-% | B wt.-% | C wt.-% |
|---|---|---|---|---|---|
| A | Emulgade SE PF | Glycerylstearate, cetearylalcohol, cetyl Palmitate | 6.00 | 6.00 | 6.00 |
| | Lanette O | Cetearylalcohol | 1.50 | 1.50 | 1.50 |
| | Cetiol V | Decyl Oleate | 4.00 | 4.00 | 4.00 |
| | Cetiol 868 | Ethylhexyl stearate | 8.00 | 8.00 | 8.00 |
| | Shea Butter | *Butyrospermum parkii* | 3.00 | 3.00 | 3.00 |
| B | Water | Aqua | Ad 100 | Ad 100 | Ad 100 |
| | 1,2-Propylene glycol | Propylene glycol | 2.64 | 2.64 | 2.64 |
| | Germaben 2 | Propylene glycol, diazolidenyl urea Methyl paraben, propyl paraben | 0.44 | 0.44 | 0.44 |
| | Neo Heliopan Hydro | Phenylbenzimidazole sulfonic acid | 3.30 | 3.30 | 3.30 |
| | Lysine | | 2.00 | 0.0 | 0.0 |
| | Triethanolamine | | 0.0 | 1.65 | 0.0 |
| | Sodium Hydroxide | | 0.0 | 0.0 | 4.55 |
| | pH after manufacturing | | 6.2 | 6.2 | 6.2 |

Example 2b

| | Ingredient: | INCI | A wt.-% | B wt.-% | C wt.-% |
|---|---|---|---|---|---|
| A | Emulgade SE PF | Glycerylstearate, cetearylalcohol, cetyl Palmitate | 6.00 | 6.00 | 6.00 |
| | Lanette O | Cetearylalcohol | 1.50 | 1.50 | 1.50 |
| | Cetiol V | Decyl Oleate | 4.00 | 4.00 | 4.00 |
| | Cetiol 868 | Ethylhexyl stearate | 8.00 | 8.00 | 8.00 |
| | Shea Butter | *Butyrospermum parkii* | 3.00 | 3.00 | 3.00 |
| B | Water | Aqua | Ad 100 | Ad 100 | Ad 100 |
| | 1,2-Propylene glycol | Propylene glycol | 2.64 | 2.64 | 2.64 |
| | Germaben 2 | Propylene glycol, diazolidenyl urea Methyl paraben, propyl paraben | 0.44 | 0.44 | 0.44 |
| | Neo Heliopan Hydro | Phenylbenzimidazole sulfonic acid | 3.30 | 3.30 | 3.30 |
| | Lysine | | 2.1 | 0.0 | 0.0 |
| | Triethanolamine | | 0.0 | 1.7 | 0.0 |
| | Sodium Hydroxide | | 0.0 | 0.0 | 4.7 |
| | pH after manufacturing | | 6.5 | 6.5 | 6.5 |

Example 2c

| | Ingredient: | INCI | A wt.-% | B wt.-% | C wt.-% |
|---|---|---|---|---|---|
| A | Emulgade SE PF | Glycerylstearate, cetearylalcohol, cetyl Palmitate | 6.00 | 6.00 | 6.00 |
| | Lanette O | Cetearylalcohol | 1.50 | 1.50 | 1.50 |
| | Cetiol V | Decyl Oleate | 4.00 | 4.00 | 4.00 |
| | Cetiol 868 | Ethylhexyl stearate | 8.00 | 8.00 | 8.00 |
| | Shea Butter | *Butyrospermum parkii* | 3.00 | 3.00 | 3.00 |
| B | Water | Aqua | Ad 100 | Ad 100 | Ad 100 |
| | 1,2-Propylene glycol | Propylene glycol | 2.64 | 2.64 | 2.64 |
| | Germaben 2 | Propylene glycol, diazolidenyl urea Methyl paraben, propyl paraben | 0.44 | 0.44 | 0.44 |
| | Neo Heliopan Hydro | Phenylbenzimidazole sulfonic acid | 3.30 | 3.30 | 3.30 |
| | Lysine | | 2.2 | 0.0 | 0.0 |
| | Triethanolamine | | 0.0 | 2.0 | 0.0 |
| | Sodium Hydroxide | | 0.0 | 0.0 | 4.8 |
| | pH after manufacturing | | 7.0 | 7.0 | 7.0 |

Manufacturing Procedure.

Ingredients of phase A were mixed and heated with stirring at 80° C. The ingredients of phase A were mixed together and heated at 80° C. with vigorous stirring until all of the phenylbenzimidazole sulfonic acid had been neutralised and dissolved into solution. Phases A & B were then mixed together with stirring and allowed to cool to room temperature and put into storage test.

Results. No crystallisation of Phenylbenzimidazole sulfonic acid was observed after manufacture of emulsions 2c-A, B & C after 1 month storage at 5° C. and ambient temperature (22° C.)

Crystallisation of phenylbenzimidazole sulfonic acid was seen in all other emulsions except for 2a-A and 2b-A after the same time period.

In the above examples 1 and 2, the salts of phenylbenzimidazole sulfonic acid can be prepared as an aqueous premix and added to phase B.

Example 3a

|   | Ingredient: | INCI | A wt.-% | B wt.-% | C wt.-% |
|---|---|---|---|---|---|
| A | Emulgade SE PF | Glycerylstearate, cetearylalcohol, cetyl Palmitate | 6.00 | 6.00 | 6.00 |
|   | Lanette O | Cetearylalcohol | 1.50 | 1.50 | 1.50 |
|   | CetioL V | Decyl Oleate | 4.00 | 4.00 | 4.00 |
|   | Cetiol 868 | Ethylhexyl stearate | 8.00 | 8.00 | 8.00 |
|   | Shea Butter | *Butyrospermum parkii* | 3.00 | 3.00 | 3.00 |
| B | Water | Aqua | Ad 100 | Ad 100 | Ad 100 |
|   | 1,2-Propylene glycol | Propylene glycol | 2.64 | 2.64 | 2.64 |
|   | Germaben 2 | Propylene glycol, diazolidenyl urea Methyl paraben, propyl paraben | 0.44 | 0.44 | 0.44 |
|   | Neo Heliopan Hydro | Phenylbenzimidazole sulfonic acid | 3.30 | 3.30 | 3.30 |
|   | Histidine |  | 2.5 | 0.0 | 0.0 |
|   | Triethanolamine |  | 0.0 | 1.6 | 0.0 |
|   | Sodium Hydroxide |  | 0.0 | 0.0 | 4.5 |
|   | pH after manufacturing |  | 6.1 | 6.0 | 6.0 |

Example 3b

|   | Ingredient: | INCI | A wt.-% | B wt.-% | C wt.-% |
|---|---|---|---|---|---|
| A | Emulgade SE PF | Glycerylstearate, cetearylalcohol, cetyl Palmitate | 6.00 | 6.00 | 6.00 |
|   | Lanette O | Cetearylalcohol | 1.50 | 1.50 | 1.50 |
|   | CetioL V | Decyl Oleate | 4.00 | 4.00 | 4.00 |
|   | Cetiol 868 | Ethylhexyl stearate | 8.00 | 8.00 | 8.00 |
|   | Shea Butter | *Butyrospermum parkii* | 3.00 | 3.00 | 3.00 |
| B | Water | Aqua | Ad 100 | Ad 100 | Ad 100 |
|   | 1,2-Propylene glycol | Propylene glycol | 2.64 | 2.64 | 2.64 |
|   | Germaben 2 | Propylene glycol, diazolidenyl urea Methyl paraben, propyl paraben | 0.44 | 0.44 | 0.44 |
|   | Neo Heliopan Hydro | Phenylbenzimidazole sulfonic acid | 3.30 | 3.30 | 3.30 |
|   | Histidine |  | 2.55 | 0.0 | 0.0 |
|   | Triethanolamine |  | 0.0 | 1.7 | 0.0 |
|   | Sodium Hydroxide |  | 0.0 | 0.0 | 4.7 |
|   | pH after manufacturing |  | 6.5 | 6.5 | 6.5 |

Example 3c

|   | Ingredient: | INCI | A wt.-% | B wt.-% | C wt.-% |
|---|---|---|---|---|---|
| A | Emulgade SE PF | Glycerylstearate, cetearylalcohol, cetyl Palmitate | 6.00 | 6.00 | 6.00 |
|   | Lanette O | Cetearylalcohol | 1.50 | 1.50 | 1.50 |
|   | CetioL V | Decyl Oleate | 4.00 | 4.00 | 4.00 |
|   | Cetiol 868 | Ethylhexyl stearate | 8.00 | 8.00 | 8.00 |
|   | Shea Butter | *Butyrospermum parkii* | 3.00 | 3.00 | 3.00 |
| B | Water | Aqua | Ad 100 | Ad 100 | Ad 100 |
|   | 1,2-Propylene glycol | Propylene glycol | 2.64 | 2.64 | 2.64 |
|   | Germaben 2 | Propylene glycol, diazolidenyl urea Methyl paraben, propyl paraben | 0.44 | 0.44 | 0.44 |

| Ingredient: | INCI | A wt.-% | B wt.-% | C wt.-% |
|---|---|---|---|---|
| Neo Heliopan Hydro | Phenylbenzimidazole sulfonic acid | 3.30 | 3.30 | 3.30 |
| Histidine | | 2.60 | 0.0 | 0.0 |
| Triethanolamine | | 0.0 | 2.0 | 0.0 |
| Sodium Hydroxide | | 0.0 | 0.0 | 4.8 |
| pH after manufacturing | | 7.0 | 7.0 | 7.0 |

Manufacturing Procedure.

Ingredients of phase A were mixed and heated with stirring at 80° C. The ingredients of phase A were mixed together and heated at 80° C. with vigorous stirring until all of the phenylbenzimidazole sulfonic acid had been neutralised and dissolved into solution. Phases A & B were then mixed together with stirring and allowed to cool to room temperature and put into storage test.

Results. No crystallisation of Phenylbenzimidazole sulfonic acid was observed after manufacture of emulsions 3c-A, B & C after 1 month storage at 5° C. and ambient temperature (22° C.).

Crystallisation of phenylbenzimidazole sulfonic acid was seen in all other emulsions except for 3a-A and 3b-A after the same time period.

Example 4a

| | Ingredient: | INCI | A wt.-% | B wt.-% | C wt.-% |
|---|---|---|---|---|---|
| A | Emulgade SE PF | Glycerylstearate, cetearylalcohol, cetyl Palmitate | 6.00 | 6.00 | 6.00 |
| | Lanette O | Cetearylalcohol | 1.50 | 1.50 | 1.50 |
| | Cetiol V | Decyl Oleate | 4.00 | 4.00 | 4.00 |
| | Cetiol 868 | Ethylhexyl stearate | 8.00 | 8.00 | 8.00 |
| | Shea Butter | *Butyrospermum parkii* | 3.00 | 3.00 | 3.00 |
| B | Water | Aqua | Ad 100 | Ad 100 | Ad 100 |
| | 1,2-Propylene glycol | Propylene glycol | 2.64 | 2.64 | 2.64 |
| | Germaben 2 | Propylene glycol, diazolidenyl urea Methyl paraben, propyl paraben | 0.44 | 0.44 | 0.44 |
| | Neo Heliopan Hydro | Phenylbenzimidazole sulfonic acid | 3.30 | 3.30 | 3.30 |
| | Ornithine | | 2.2 | 0.0 | 0.0 |
| | Triethanolamine | | 0.0 | 1.6 | 0.0 |
| | Sodium Hydroxide | | 0.0 | 0.0 | 4.5 |
| | pH after manufacturing | | 6.0 | 6.0 | 6.0 |

Example 4b

| | Ingredient: | INCI | A wt.-% | B wt.-% | C wt.-% |
|---|---|---|---|---|---|
| A | Emulgade SE PF | Glycerylstearate, cetearylalcohol, cetyl Palmitate | 6.00 | 6.00 | 6.00 |
| | Lanette O | Cetearylalcohol | 1.50 | 1.50 | 1.50 |
| | Cetiol V | Decyl Oleate | 4.00 | 4.00 | 4.00 |
| | Cetiol 868 | Ethylhexyl stearate | 8.00 | 8.00 | 8.00 |
| | Shea Butter | *Butyrospermum parkii* | 3.00 | 3.00 | 3.00 |
| B | Water | Aqua | Ad 100 | Ad 100 | Ad 100 |
| | 1,2-Propylene glycol | Propylene glycol | 2.64 | 2.64 | 2.64 |
| | Germaben 2 | Propylene glycol, diazolidenyl urea Methyl paraben, propyl paraben | 0.44 | 0.44 | 0.44 |
| | Neo Heliopan Hydro | Phenylbenzimidazole sulfonic acid | 3.30 | 3.30 | 3.30 |
| | Ornithine | | 2.35 | 0.0 | 0.0 |
| | Triethanolamine | | 0.0 | 1.7 | 0.0 |
| | Sodium Hydroxide | | 0.0 | 0.0 | 4.65 |
| | pH after manufacturing | | 6.5 | 6.5 | 6.5 |

Example 4c

| | Ingredient: | INCI | A wt.-% | B wt.-% | C wt.-% |
|---|---|---|---|---|---|
| A | Emulgade SE PF | Glycerylstearate, cetearylalcohol, cetyl Palmitate | 6.00 | 6.00 | 6.00 |
| | Lanette O | Cetearylalcohol | 1.50 | 1.50 | 1.50 |
| | Cetiol V | Decyl Oleate | 4.00 | 4.00 | 4.00 |
| | Cetiol 868 | Ethylhexyl stearate | 8.00 | 8.00 | 8.00 |
| | Shea Butter | *Butyrospermum parkii* | 3.00 | 3.00 | 3.00 |

-continued

| Ingredient: | INCI | A wt.-% | B wt.-% | C wt.-% |
|---|---|---|---|---|
| B Water | Aqua | Ad 100 | Ad 100 | Ad 100 |
| 1,2-Propylene glycol | Propylene glycol | 2.64 | 2.64 | 2.64 |
| Germaben 2 | Propylene glycol, diazolidenyl urea Methyl paraben, propyl paraben | 0.44 | 0.44 | 0.44 |
| Neo Heliopan Hydro | Phenylbenzimidazole sulfonic acid | 3.30 | 3.30 | 3.30 |
| Ornithine | | 2.5 | 0.0 | 0.0 |
| Triethanolamine | | 0.0 | 2.0 | 0.0 |
| Sodium Hydroxide | | 0.0 | 0.0 | 4.75 |
| pH after manufacturing | | 7.0 | 7.0 | 7.0 |

Manufacturing Procedure.

Ingredients of phase A were mixed and heated with stirring at 80° C. The ingredients of phase A were mixed together and heated at 80° C. with vigorous stirring until all of the phenylbenzimidazole sulfonic acid had been neutralised and dissolved into solution. Phases A & B were then mixed together with stirring and allowed to cool to room temperature and put into storage test.

Results. No crystallisation of Phenylbenzimidazole sulfonic acid was observed after manufacture of emulsions 4c-A, B & C after 1 month storage at 5° C. and ambient temperature (22° C.).

Crystallisation of phenylbenzimidazole sulfonic acid was seen in all other emulsions except for 4a-A and 4b-A after the same time period.

FORMULATION EXAMPLES

Formulation Example 1

Sunscreen Soft Cream (O/W), In-Vitro SPF 5, Water Resistant

| Part | Raw Materials | INCI Name | % (wt.) |
|---|---|---|---|
| A | Emulsiphos | Potassium Cetyl Phosphate, Hydrogenated Palm Glycerides | 1.50 |
| | Cutina GMS/V | Glyceryl Stearate | 2.00 |
| | Copherol 1250 | Tocopheryl Acetate | 0.50 |
| | Lanette 16 | Cetyl Alcohol | 1.00 |
| | Tegosoft TN | C 12-15 Alkyl Benzoate | 24.00 |
| | Prisorine 3505 | Isostearic Acid | 1.00 |
| B | Water, dist. | Water (Aqua) | Ad 100 |
| | Neo Heliopan ® Hydro | Phenylbenzimidazole Sulfonic Acid | 3.0 |
| | Lysine | Lysine | 2.10 |
| | EDETA B liq. | Tetrasodium EDTA | 0.20 |
| | Glycerol, 99% | Glycerin | 3.00 |
| | Phenoxyethanol | Phenoxyethanol | 0.70 |
| | Solbrol M | Methylparaben | 0.20 |
| | Solbrol P | Propylparaben | 0.10 |
| | Carbopol ETD 2050 | Carbomer | 0.20 |
| C | Perfume oil | Parfum (Fragrance) | 0.30 |

Manufacturing Procedure.

Part A: Heat to about 85° C.

Part B: Weigh in raw materials without Carbopol. Disperse Carbopol therein using Ultra Turrax. Heat to about 85° C. Add B to A. and then homogenise while hot (Ultra Turrax). Leave to cool with stirring.

Part C: Add to A/B at 30° C. or less with stirring pH-value of emulsion 6.2.

Formulation Example 2

Sunscreen Lotion (O/W), In-Vitro SPF 20

| Part | Raw Materials | INCI Name | % (wt.) |
|---|---|---|---|
| A | Emulsiphos | Potassium Cetyl Phosphate, Hydrogenated Palm Glycerides | 1.50 |
| | Cutina GMS/V | Glyceryl Stearate | 2.00 |
| | Copherol 1250 | Tocopheryl Acetate | 0.50 |
| | Lanette 16 | Cetyl Alcohol | 1.00 |
| | Tegosoft TN | C 12-15 Alkyl Benzoate | 10.60 |
| | Prisorine 3505 | Isostearic Acid | 1.00 |
| | Neo Heliopan ® 357 | Butyl Methoxydibenzolymethane | 2.00 |
| | Neo Heliopan ® AV | Ethylhexyl Methoxycinnamate | 5.00 |
| | EDETA BD | Disodium EDTA | 0.10 |
| | Carbopol ETD 2050 | Carbomer | 0.20 |
| B | Water, dist. | Water (Aqua) | Ad 100 |
| | Glycerol, 99% | Glycerin | 3.00 |
| | Dragocid Liquid | Phenoxyethanol, Methylparaben, Ethylparaben, Butylparaben, Propylparaben, Isobutylparaben | 0.80 |
| C | L-Arginine CG | Arginine | 0.40 |
| | Neo Heliopan ® Hydro, 25% strength solution neutralised with Arginine | Phenylbenzimidazole Sulfonic Acid, arginine | 8.00 |
| D | Perfume oil | Parfum (Fragrance) | 0.30 |

Manufacturing Procedure.

Part A: Heat to about 85° C.

Part B: Weigh in raw materials without Carbopol. Disperse Carbopol therein using Ultra Turrax. Heat to about 85° C. Add B to A.

Part C: Immediately add to A/B and then homogenise while hot (Ultra Turrax). Leave to cool with stirring.

Part D: Add and stir in.

pH-value of emulsion 6.0

Formulation Example 3

Low oil Content Sunscreen Milk (O/W), In-Vitro SPF 25

| Part | Raw Materials | INCI Name | A % (wt.) | B % (wt.) |
|---|---|---|---|---|
| A | Tegin M | Glyceryl Stearate | 2.50 | 2.50 |
| | Tagat S | PEG-30 Glyceryl Stearate | 1.95 | 1.95 |
| | Lanette O | Cetearyl Alcohol | 2.20 | 2.20 |

-continued

| Part | Raw Materials | INCI Name | A % (wt.) | B % (wt.) |
|---|---|---|---|---|
| | Copherol 1250 | Tocopheryl Acetate | 0.50 | 0.50 |
| | Phenonip | Phenoxyethanol (and) methylparaben (and) Butylparaben (and) ethylparaben (and) Propylparaben | 0.15 | 0.15 |
| | Neo Heliopan ® AV | Ethylhexyl Methoxycinnamate | 5.00 | 5.00 |
| | Neo Heliopan ® 303 | Octocrylene | 5.00 | 5.00 |
| | Neo Heliopan ® 357 | Butyl Methoxydibenzolymethane | 2.00 | 2.00 |
| | EDETA BD | Disodium EDTA | 0.10 | 0.10 |
| | Carbopol 2050 | Carbomer | 0.40 | 0.40 |
| B | Water, dist. | Water (Aqua) | Ad 100 | Ad 100 |
| | Neo Heliopan ® Hydro | Phenylbenzimidazole Sulfonic Acid | 3.30 | 3.30 |
| | Neo Heliopan ® AP | Disodium Phenyl Dibenzimidazole Tetrasulfonate, arginine | 2.20 | 2.20 |
| | Arginine | Arginine | 3.50 | 2.86 |
| | 1,2-Propylene glycol | Propylene Glycol | 2.00 | 2.00 |
| | Phenonip | Phenoxyethanol (and) Methylparaben (and) Butylparaben (and) Ethylparaben (and) Propylparaben | 0.30 | 0.30 |
| C | Water, dist. | Water (Aqua) | 19.00 | 19.00 |
| | NaOH, 10% strength | Sodium Hydroxide | 0.00 | 1.70 |
| D | Perfume oil | Parfum (Fragrance) | 0.30 | 0.30 |
| | pH after manufacturing | | 6.0 | 6.5 |

Manufacturing Procedure.
Part A: Heat to 80-85° C.
Part B: Heat to 80-85° C., Add part B to part A with stirring.
Part C: Disperse Carbopol into the water and neutralise with NaOH, with stirring. Add part C at about 60° C. with stirring. Allow to cool to RT.
Part D: Add and stir.

Formulation Example 4

Sunscreen Lotion (O/W), In-Vitro SPF 18

| Part | Raw Materials | INCI Name | % (wt.) |
|---|---|---|---|
| A | Eumulgin VL 75 | Lauryl Glucoside (and) Polyglyceryl-2-Dipolyhydroxystearate (and) Glycerin | 3.00 |
| | Tegosoft TN | C12-25 Alkyl Benzoate | 20.00 |
| | Copherol 1250 | Tocopheryl Acetate | 0.50 |
| | Perfume oil | Parfum (Fragrance) | 0.20 |
| | Neo Heliopan ® 357 | Butyl Methoxydibenzolymethane | 2.00 |
| | Neo Heliopan ® E1000 | Isoamyl p-Methoxycinnamate | 5.00 |
| | Neo Heliopan ® 303 | Octocrylene | 5.00 |
| | Carbopol 2050 ETD | Carbomer | 0.35 |
| | Pemulen TR-1 | Acrylates/C10-30 Alkyl Acrylate Cross-polymer | 0.15 |
| | EDETA BD | Disodium EDTA | 0.10 |
| B | Water, dist. | Water (Aqua) | Ad 100 |
| | Glycerol, 99% | Glycerin | 5.00 |
| | Dragocid Liquid | Phenoxyethanol, Methylparaben, Ethylparaben, Butylparaben, Propylparaben, Isobutylparaben | 0.80 |
| | Neo Heliopan ® Hydro | Phenylbenzimidazole Sulfonic Acid | 2.00 |
| | Histidine | Histidine | 2.30 |

Manufacturing Procedure.
Part A: Dissolve the solids in the oils and liquid UV filters (heating to about 70° C.). Allow to cool to about 30° C., add the remaining constituents apart from Carbopol and Pemulen and mix at room temperature (stir for about 5 minutes). Stir in Carbopol and Pemulen. in Part B: Add water and glycerol, then disperse Neo Heliopan® Hydro with vigorous stirring and heating to 70° C., add histidine until all of the Neo Heliopan® Hydro has been dissolved and add all of part B to part A with stirring. Stir for about 60 minutes with cooling and. homogenise using the Ultra Turrax.

pH-value of emulsion 6.2.

Formulation Example 5

Sunscreen Cream (W/O), In-Vitro SPF 10, Water Resistant

| Part | Raw Materials | INCI Name | % (wt.) |
|---|---|---|---|
| A | Dehymuls PGPH | Polyglyceryl-2 Dipolyhydroxystearate | 5.00 |
| | Copherol 1250 | Tocopheryl Acetate | 0.50 |
| | Permulgin 3220 | Ozokerite | 0.50 |
| | Aluminium stearate | Aluminium Stearate | 0.50 |
| | Tegosoft TN | C12-15 Alkyl Benzoate | 25.00 |
| | Neo Heliopan ® 357 | Butyl Methoxydibenzolymethane | 2.00 |
| | EDETA BD | Disodium EDTA | 0.10 |
| B | Water, dist. | Water (Aqua) | Ad 100 |
| | Glycerin, 99% | Glycerin | 4.00 |
| | Dragocid Liquid | Phenoxyethanol, Methylparaben, Ethylparaben, Butylparaben, Propylparaben, Isobutylparaben | 1.00 |
| | Neo Heliopan ® Hydro, 25% strength solution neutralised with Arginine | Phenylbenzimidazole Sulfonic Acid, Arginine | 20.00 |
| | Lysine | Lysine | 0.20 |
| | Magnesium sulfate | Magnesium Sulfate | 0.50 |

Manufacturing Procedure.
Part A: Heat to about 85° C.
Part B: Heat to about 85° C. Add B to A. Allow to cool with stirring then homogenise.

Formulation Example 6

Sunscreen Soft Cream (W/O), In-Vitro SPF 50

| Part | Raw Materials | INCI Name | % (wt.) |
|---|---|---|---|
| A | Dehymuls PGPH | Polyglyceryl-2 Dipolyhydroxystearate | 5.00 |
|  | Copherol 1250 | Tocopheryl Acetate | 0.50 |
|  | Permulgin 3220 | Ozokerite | 0.50 |
|  | Zinc stearate | Zinc Stearate | 0.50 |
|  | Tegosoft TN | C12-15 Alkyl Benzoate | 10.00 |
|  | Neo Heliopan ® BB | Benzophenone-3 | 3.00 |
|  | Neo Heliopan ® HMS | Homosalate | 5.00 |
|  | Neo Heliopan ® 303 | Octocrylene | 5.00 |
|  | Neo Heliopan ® OS | Ethylhexyl Salicylate | 5.00 |
|  | Uvinul ® T-150 | Ethylhexyl Triazone | 3.00 |
|  | Zinc oxide neutral | Zinc Oxide | 5.00 |
| B | Water, dist. | Water (Aqua) | Ad 100 |
|  | EDETA BD | Disodium EDTA | 0.10 |
|  | Glycerol | Glycerin | 4.00 |
|  | Dragocid Liquid | Phenoxyethanol, Methylparaben, Ethylparaben, Butylparaben, Propylparaben, Isobutylparaben | 1.00 |
|  | Neo Heliopan ® Hydro, 20% strength solution neutralised with Lysine | Phenylbenzimidazole Sulfonic Acid, Lysine | 10.00 |
|  | Arginine | Arginine | 0.15 |
|  | Magnesium sulfate | Magnesium Sulfate | 0.50 |
| C | Parfume oil | Parfum (Fragrance) | 0.20 |

Manufacturing Procedure.

Part A: Heat to about 85° C.

Part B: Heat to about 85° C. (without zinc oxide; disperse zinc oxide therein using the Ultra Turrax). Add B to A. Allow to cool with stirring.

Part C: Add and then homogenise.

Formulation Example 7

Day Care Cream with Broad Spectrum UV Protection

| Part | Raw Materials | INCI Name | % (wt.) |
|---|---|---|---|
| A | Emulgade PL 68/50 | Cetearyl Glycoside (and) Cetearyl Alcohol | 4.50 |
|  | Cetiol PGL | Hexyldecanol (and) Hexyldecyl Laurate | 8.00 |
|  | Myritol 331 | Cocoglycerides | 8.00 |
|  | Copherol 1250 | Tocopheryl Acetate | 0.50 |
|  | Neo Heliopan ® 303 | Octocrylene | 3.00 |
|  | Neo Heliopan ® OS | Ethylhexyl Salicylate | 5.00 |
| B | Water, dist. | Water (Aqua) | Ad 100 |
|  | Aqueous mixture of 15% Neo Heliopan ® Hydro and 10% Neo Heliopan ® AP neutralised with Arginine | Phenylbenzimidazole Sulfonic Acid, Disodium Phenyl Dibenzimidazole Tetrasulfonate, Arginine | 22.00 |
|  | Glycerol | Glycerin | 3.00 |
| C | Dragocide Liquid | Phenoxyethanol (and) Methylparaben (and) Butyparaben (and) Ethyparaben (and) Propylparaben | 0.50 |
|  | Water, dist. | Water (Aqua) | 25.00 |
|  | Carbopol ETD 2050 | Carbomer | 0.20 |
|  | Arginine | Arginine | 0.40 |
| D | Perfume oil | Parfum (Fragrance) | 0.30 |

Manufacturing Procedure.

Part A: Heat to 80° C.

Part B: Heat to 80° C. Add to part A with stirring.

Part C: Disperse Carbopol in water and neutralise with sodium hydroxide solution. Add to part NB at about 55° C. pH-value of emulsion 6.1.

Formulation Example 8

Sunscreen Spray In-Vitro SPF 20

| Part | Raw Materials | INCI Name | % (wt.) |
|---|---|---|---|
| A | Water, demin. | Water (Aqua) | Ad 100 |
|  | Glycerol, 99% | Glycerin | 4.00 |
|  | Hydrolyte 5 | 1,2-Pentylene Glycol | 5.00 |
|  | D-Panthenol | Panthenol | 0.50 |
|  | Lara Care A-200 | Galactoarabinan | 0.25 |
| B | Baysilone oil M 10 | Dimethicone | 1.00 |
|  | Edeta BD | Disodium EDTA | 0.10 |
|  | Copherol 1250 | Tocopheryl Acetate | 0.50 |
|  | Cetiol OE | Dicaprylyl Ether | 3.00 |
|  | Neo Heliopan ® HMS | Homosalate | 5.00 |
|  | Neo Heliopan ® AV | Ethylhexyl Methoxycinnamate | 6.00 |
|  | Neo Heliopan ® 357 | Butyl Methoxydibenzoylmethane | 1.00 |

| Part | Raw Materials | INCI Name | % (wt.) |
|---|---|---|---|
| | Tinosorb ® S | Bis Ethylhexyloxyphenol Methoxyphenyl Triazine | 2.00 |
| | alpha-Bisabolol | Bisabolol | 0.10 |
| | Pemulen TR-2 | Acrylates/C10-30 Alkyl Acrylate Crosspolymer | 0.25 |
| C | Phenoxyethanol | Phenoxyethanol | 0.70 |
| | Solbrol M | Methylparaben | 0.20 |
| | Solbrol P | Propylparaben | 0.10 |
| | Neo Heliopan ® Hydro, 25% strength solution neutralised with Arginine | Phenylbenzimidazole Sulfonic Acid, arginine | 8.00 |
| | Arginine | Arginine | 0.40 |
| D | Perfume oil | Fragrance (Parfum) | 0.20 |

Manufacturing Procedure.

Part A: Dissolve Lara Care A-200 into the other constituents of part A with stirring.

Part B: Weigh in all raw materials (without Pemulen) and dissolve the crystalline substances with heating. Disperse Pemulen therein. Add part B to part A then homogenise for 1 minute.

Add part C+D and homogenise again for 1-2 minutes using the Ultra Turrax.

pH-value of formulation 6.1.

Formulation Example 9

Sunscreen Hydrodispersion Gel (Balm)

| Part | Raw Materials | INCI Name | % (wt.) |
|---|---|---|---|
| A | Water, dist. | Water (Aqua) | Ad 100 |
| | Carbopol Ultrez 21 | Acrylates/C10-30 Alkyl Acrylate Crosspolymer | 1.00 |
| | Triethanolamine | Triethanolamine | 1.20 |
| | Lysine | Lysine | 1.50 |
| B | Neo Heliopan ® Hydro, 20% strength solution neutralised with Lysine | Phenylbenzimidazole Sulfonic Acid, Lysine | 10.00 |
| C | Neo Heliopan ® E1000 | Isoamyl p-I Methoxycinnamate | 3.00 |
| | Neo Heliopan ® 357 | Butyl Methoxydibenzoylmethane | 2.00 |
| | Isopropyl myristate | Isopropyl Myristate | 4.00 |
| | Baysilone oil PK 20 | Phenyl Trimethicone | 3.00 |
| | Dragocide Liquid | Phenoxyethanol (and) Methylparaben (and) Butyparaben (and) Ethyparaben (and) Propylparaben | 0.50 |
| | Perfume oil | Parfum (Fragrance) | 0.30 |
| | Edeta BD | Disodium EDTA | 0.10 |
| | Alpha Bisabolol | Alpha Bisabolol | 0.10 |

Manufacturing Procedure.

Part A: Disperse Carbopol in water and neutralise with triethanolamine solution.

Part B: Add to part A with stirring.

Part C: Dissolve crystalline constituents in the other raw materials of part C with warming (max. 40° C.) and add to part A/B. Stir well and then homogenise. (Homozenta).

pH-value of formulation 6.2.

Formulation Example 10

Hair Conditioner with UV Filters

| Part | Raw Materials | INCI Name | % (wt.) |
|---|---|---|---|
| A | Lanette O | Cetearyl Alcohol | 4.0 |
| | Dragoxat 89 | Ethylhexyl Isononanoate | 4.0 |
| | Emulsiphos | Potassium Cetyl Phosphate, Hydrogenated Palm Glycerides | 0.50 |
| B | Natrosol 250 HR | Hydroxyethylcellulose | 0.25 |
| | Water, dist. | Water (Aqua) | Ad 100 |
| | Neo Heliopan ® Hydro | Phenylbenzimidazole Sulfonic Acid | 2.00 |
| | L-Arginine | Arginine | 1.23 |
| | Edeta BD | Disodium EDTA | 0.05 |
| | Dragocide Liquid | Phenoxyethanol (and) Methylparaben (and) Butyparaben (and) Ethyparaben (and) Propylparaben | 0.80 |

-continued

| Part | Raw Materials | INCI Name | % (wt.) |
|---|---|---|---|
| C | Dow Corning 949 Cationic Emulsion | Amodimethicone, Cetrimonium Chloride, Trideceth-12 | 2.00 |
|  | Dow Corning 5200 | Laurylmethicone Copolyol | 0.50 |
|  | Perfume oil | Parfum (Fragrance) | 0.80 |

Manufacturing Procedure.
Part A: Heat to 80° C.
Part B: Swell Natrosol in water, Neo Heliopan Hydro and Arginine, add Dragocid Liquid and heat to 80° C. Add to part A with stirring and emulsify. Coll down with stirring.
Part C: Add at 35° C. and cool to RT with stirring.
pH-value: 6.1

Formulation Example 11

Broad Spectrum Aqueous Gel In-Vitro SPF 12.0

|  | Ingredients | INCI-Name | % |
|---|---|---|---|
| A | Demineralised Water | Water (Aqua) | Ad 100 |
|  | Amaze XT | Dehydroxanthan Gum | 1.00 |
| B | Demineralised Water | Water (Aqua) | 15.00 |
|  | Neo Heliopan ® Hydro | Phenylbenzimidazole Sulfonic Acid | 3.00 |
|  | Neo Heliopan ® AP | Disodium Phenyl Dibenzimidazole Tetrasulfonate | 3.00 |
|  | L-Arginine | Arginine | 3.20 |
| C | Symdiol 68 | 1,2-Hexanediol and 1,2-Octanediol | 0.50 |
|  | Hydrolite 5 | Pentylene Glycol | 2.00 |
|  | Dragoderm | Glycerin, Triticum Vulgare (Wheat) Gluten, Water (Aqua) | 2.00 |
| D | Dow Corning 193 | PEG-12 Dimethicone | 1.00 |
|  | Ethanol 96% | SD-Alcohol 39-C | 10.00 |
|  | Perfume | Fragrance | 0.10 |

Manufacturing Procedure.
Part A: Stir Amaze XT into the water with stirring until it is swollen and a gel has formed
Part B: Stir the ingredients together and add to Part A and then add Parts C with stirring until uniform and then add Part D with gentle stirring.
pH-value of formulation 6.0

The same formulation in which arginine was replaced with sodium hydroxide to neutralise the phenylbenzimidazole sulfonic acid with the formula having a pH of 7.3 gave an in-vitro SPF of 9.2. This indicates that the use of basic amines to neutralise phenylbenzimidazole sulfonic acid to a pH below 7.0 in cosmetic or dermatological preparations boosts the sun protection of the formulation compared to other neutralisation bases in which the pH-value of the emulsion is greater than 7.0.

Formulation Examples 12

Water Resistant Broad Spectrum O/W Emulsions
In-Vitro SPF 50+

|  | Ingredients | INCI | A % w/w | B % w/w | C % w/w |
|---|---|---|---|---|---|
| A | Emulsiphos | Potassium Cetyl Phosphate, Hydrogenated Palm Glycerides | 3.50 | 3.50 | 3.50 |
|  | Lanette O | Cetearylalcohol | 1.00 | 1.00 | 1.00 |
| B | Neo Heliopan ® HMS | Homosalate | 5.00 | 5.00 | 5.00 |
|  | Neo Heliopan ® 303 | Octocrylene | 10.00 | 10.00 | 10.00 |
|  | Neo Heliopan ® OS | Ethylhexyl Salicylate | 5.00 | 5.00 | 5.00 |
|  | Neo Heliopan ® 357 | Butyl Methoxydibenzoylmethane | 5.00 | 4.50 | 5.00 |
|  | Eusolex ® T2000 | Titanium Dioxide, Alumina, Simethicone | 4.00 | 4.00 | 4.00 |
|  | Tinosorb ® S | Bis Ethylhexyloxyphenol Methoxyphenyl Triazine | 0.00 | 4.50 | 3.00 |
|  | Abil Wax 9801 | Cetyl Dimethicone | 1.00 | 1.00 | 1.00 |
|  | Silcare Silicone 41M65 | Stearyl Dimethicone | 1.00 | 1.00 | 1.00 |
|  | Baysilone oil PK 20 | Phenyl Trimethicone | 2.00 | 2.00 | 2.00 |
|  | Isoadipat | Diisopropyladipate | 2.00 | 2.00 | 2.00 |
|  | Tocopherylacetat | Tococpheryl Acetate | 0.50 | 0.50 | 0.50 |
|  | Antaron V216 | VP/Hexadecene Copolymer | 0.50 | 0.50 | 0.50 |
|  | EDTA BD | Disodium EDTA | 0.10 | 0.10 | 0.10 |
|  | Keltrol T | Xanthan Gum | 0.50 | 0.50 | 0.50 |
|  | Water demineralised | Water (Aqua) | Ad 100 | Ad 100 | Ad 100 |
|  | Neo Heliopan ® Hydro | Phenylbenzimidazole Sulfonic Acid | 2.00 | 2.00 | 2.00 |
|  | Neo Heliopan ® AP | Disodium Phenyl Dibenzimidazole Tetrasulfonate | 2.00 | 0.00 | 1.00 |
|  | Phenonip | Phenoxyethanol (and) Methylparaben (and) Butyparaben (and) Ethyparaben (and) Propylparaben | 0.70 | 0.70 | 0.70 |
|  | Arginine | Arginine | 2.20 | 1.15 | 1.65 |
|  | Lara Care A-200 | Galactoarabinan | 0.25 | 0.25 | 0.25 |
|  | Hydrolite 5 | Pentylene Glycol | 3.00 | 3.00 | 3.00 |
| C | Fragrance | Fragrance (parfum) | 0.30 | 0.30 | 0.30 |
|  | pH |  | 6.0 | 6.1 | 6.1 |

Manufacturing Procedure.

Part A: Heat all components except for the Xanthan Gum and TiO2 to 85° C. The add Xanthan Gum and TiO2 and homogenise.

Part B: Heat all components to 85° C. and add to Part A with stirring, stir to room temperature.

Part C: Add Part C to Parts A & B and homogenise.

Formulation Examples 13 Sunspray O/W exp. SPF 20

| Part | Ingredients | INCI | A Wt.-% |
|---|---|---|---|
| A | Dracorin GOC | Glyceryl Oleate Citrate, Caprylic/Capric Triglyceride | 2.00 |
|  | Neo Heliopan HMS | Homosalate | 7.00 |
|  | Neo Heliopan 357 | Butyl Methoxydibenzoylmethane | 4.00 |
|  | Neo Heliopan OS | Ethylhexyl Salicylate | 5.00 |
|  | Isoadipat |  | 6.00 |
|  | Corapan TQ | Diethylhexyl 2.6 Naphthalate | 3.00 |
|  | Edeta BD | Disodium EDTA | 0.10 |
|  | Vitamin E Acetat | Tocopheryl Acetate | 0.50 |
|  | Baysilone Oil M 10 | Dimethicone | 1.00 |
|  | Alpha-Bisabolol | Bisabolol | 0.10 |
|  | Pemulen TR 2 | Acrylates/C10-30 Acrylates Copolymer | 0.25 |
|  | Perfume |  | 0.25 |
| B | Deion. Wasser | Water (Aqua) | Ad 100 |
|  | Glycerin 99% | Glycerin | 4.00 |
|  | Butylenglycol | Butylene Glycol | 5.00 |
|  | Dragocid Liquid | Phenoxyethanol, Methylparaben, Ethylparaben, Butylparaben, Propylparaben, Isobutylparaben | 0.80 |
|  | Neo Heliopan Hydro, used as 25% aq. solution neutralised with Arginine | Phenylbenzimidazole Sulfonic Acid | 8.00 |
| C | Arginine | Arginine | 0.47 |
|  | pH-value |  | 6.0 |

Manufacturing Procedure.

Part A: Dissolve the Neo Heliopan 357 in the other components of phase A (except for Pemulen and EDTA) by heating up to 50° C. The add Xanthan Gum and TiO2 and homogenise.

Part B: Add to Part A without stirring, then start emulsifying.

Part C: Add Part C to Parts A & B while homogenising.

Formulation Example 14

Clear Hair Shampoo with UV-Protection

|  | Ingredients | INCI-Name | % |
|---|---|---|---|
| A | Demineralised Water | Water (Aqua) | Ad 100 |
|  | Merquat 550 | Polyquaterium-7 | 0.50 |
| B | Neo Heliopan ® Hydro | Phenylbenzimidazole Sulfonic Acid | 2.00 |
|  | L-Arginine | Arginine | 1.45 |
| C | Genapol LRO Liquid | Sodium Laureth Sulfate | 30.00 |
|  | Tego Betain F 50 | Cocoamidopropyl Betaine | 5.00 |
|  | Antil 141 | Propylene Glycol, PEG-55 Propylene Glycol Dioleate | 0.80 |
|  | Dragocide Liquid 660079 | Phenoxyethanol, Methylparaben, Ethylparaben, Butylparaben, Propylparaben, Isobutylparaben | 0.80 |
|  | D-Panthenol 75 L | Panthenol | 1.00 |
|  | Extrapone ® Lime (616268) | Propylene Glycol, Water (Aqua), Citrus Aurantifolia (Lime) Juice | 1.00 |
|  | Sodium Chloride | Sodium Chloride | 0.70 |
|  | Perfume | Fragrance | 0.40 |

Manufacturing Procedure.

Part A: Dissolve Merquat in water with stirring

Part B: Add Neo Heliopan Hydro and neutralise with Arginine, dissolve until a clear solution has formed.

Part C: Add the ingredients to part AB as listed and stir until a uniform solution has formed. The viscosity can be adjusted by the amount of sodium chloride.

pH-value of formulation 6.0

Other Formulation Examples

1. O/W Emulsions: SPF>20

| RAW MATERIAL NAME (MANUFACTURER) | INCI | 1 | 2 | 3 | 4 | 5 | 6 | 7 | 8 | 9 | 10 | 11 |
|---|---|---|---|---|---|---|---|---|---|---|---|---|
| Emulsifier |  |  |  |  |  |  |  |  |  |  |  |  |
| Emulsiphos (Symrise) | Potassium Cetyl Phosphate, Hydrogenated Palm Glycerides |  |  |  |  | 2.0 |  |  |  |  |  |  |

| RAW MATERIAL NAME (MANUFACTURER) | INCI | 1 | 2 | 3 | 4 | 5 | 6 | 7 | 8 | 9 | 10 | 11 |
|---|---|---|---|---|---|---|---|---|---|---|---|---|
| Dracorin CE | Glyceryl Stearate Citrate | 1.0 | 1.0 | | | | | | | | | |
| Dracorin GOC (Symrise) | Glyceryl Oleyl Citrate | | | | | 4.0 | | | | | | |
| | Polyglyceryl 2-Dipolyhydroxystearate | 0.25 | 0.25 | | | | | | | | | |
| | Cetearyl Alcohol, Peg-40 Castor Oil, Sodium Cetearyl Sulfate | | | | | | | | 3.75 | | | |
| | PEG-30 Dipolyhydroxystearate | | | | | | | | 1.0 | | | |
| | Polyglyceryl-3 Methyl-glucose Distearate | | | | | | | | | 2.0 | | |
| | Sorbitan Stearate | | | | | 0.5 | | | 1.0 | | | |
| | Glyceryl Stearate SE | | | | | | | 1.5 | | | | |
| | Glyceryl Stearate | | | 2.5 | 1.0 | | 4.0 | | | | 4.0 | |
| | Isostearic Acid | | | | | | 1.0 | | | | | |
| | Stearic Acid | | | | 1.0 | | | | | 4.0 | | 0.5 |
| | PEG 40 Stearate | | | | 1.0 | | | | | 1.0 | | |
| | PEG 100 Stearate | | | | | | | | | | 2.0 | 0.5 |
| | Potassium Cetyl Phosphate | | | | | | 2.0 | | | | 0.5 | 2.0 |
| Lanette E ® (Cognis) | Sodium Cetearyl Sulphate | | | | | | | | | 0.5 | | |
| Emulgin B2 ® (Cognis) | Ceteareth-20 | | | | | | | 0.7 | | | 1.0 | |
| Oil Soluble UV Filters | | | | | | | | | | | | |
| Neo Heliopan ® AV (Symrise) | Ethylhexyl Methoxy-cinnamate | 8.0 | 8.0 | | | | 4.0 | | | 5.0 | | |
| Neo Heliopan ® 303 (Symrise) | Octocrylene | | | 5.0 | 5.0 | | | | 5.0 | | 2.4 | 10.0 |
| Neo Heliopan ® 357 (Symrise) | Butyl Methoxydibenzoyl-methane | 4.5 | 4.5 | 2.5 | 0.5 | 3.0 | 0.5 | 2.0 | 2.0 | | 3.0 | 3.0 |
| Neo Heliopan ® E 1000 (Symrise) | Isoamyl p-Methoxy-cinnamate | | | | 5.0 | 4.0 | | | | | | |
| Neo Heliopan ® HMS (Symrise) | Homosalate | | | 5.0 | 5.0 | | | | | 3.0 | 10.0 | |
| Neo Heliopan ® OS (Symrise) | Ethylhexyl Salicylate | | | 2.0 | 5.0 | | | | | 5.0 | 5.0 | 3.0 |
| Neo Heliopan ® MBC (Symrise) | 4-Methylbenzylidene-camphor | | | | 1.0 | | | | | | | |
| Neo Heliopan ® MA (Symrise) | Menthyl Anthranilate | | | | | | 1.0 | | | | | |
| Neo Heliopan ® BB (Symrise) | Benzophenone-3 | | | | 0.5 | | 1.0 | 0.5 | 0.5 | 4.0 | 5.0 | |
| Mexoryl ® XL | Drometrizole Trisiloxane | | | | 1.0 | | | | | | | 3.0 |
| Tinosorb ® S | Bis-Ethylhexyloxyphenol Methoxyphenyl Triazine | 0.5 | 0.5 | | 0.5 | | | | | | | |
| Uvinul ® T-150 | Ethylhexyl Triazone | 1.0 | 1.0 | 1.0 | 0.5 | | | | | | | 0.5 |
| | -Bis[5-1(dimethylpropyl)benzoxazol-2-yl-1.5 5 3 (4-phenyl)imino]-6-(2-ethylhexyl)imino-1,3,5-triazine | | | | | | | 1.0 | | | | |
| Uvinul ® A Plus | Diethylamino Hydroxy-benzoyl Hexyl Benzoate | 1.0 | 1.0 | 2.0 | 0.5 | 2.0 | | | | | | |
| Indanylidene derivatives according to DE 10055940 | | | | | 0.5 | 0.5 | | | | | | |
| Benzoylcinnamylnitrile-derivatives according to WO 2006/015954 | | | | 2.0 | 0.5 | 0.5 | | | | | | |
| Parsol SLX | Polysiloxane-15 | | | | 2.0 | | | | | | | |
| Uvasorb HEB | Diethylhexyl Butamido Triazone | | | | 0.5 | | 2.0 | | | | | |
| Benzylidene butyrolactones according to EP 1008593 | | | | | 1.0 | 2.0 | | | | | | |

-continued

| RAW MATERIAL NAME (MANUFACTURER) | INCI | 1 | 2 | 3 | 4 | 5 | 6 | 7 | 8 | 9 | 10 | 11 |
|---|---|---|---|---|---|---|---|---|---|---|---|---|
| Benzylidene-dicarbonyl compounds described in WO/2005/107692 | | | | | 0.5 | | | | | | | |
| Water Soluble UV Filters | | | | | | | | | | | | |
| Neo Heliopan ® AP (Symrise), neutralised with lysine or arginine or ornithine or histidine | Disodium Phenyl-dibenzimidazoletetra-sulphonate | | | 1.0 | 0.2 | 1.5 | | | 0.5 | | | |
| Neo Heliopan ® Hydro (Symrise) neutralised with lysine or arginine or ornithine or histidine | Phenylbenzimidazole-sulphonic Acid | 1.3 | 1.3 | 2.6 | 1.3 | 2.64 | 1.8 | 2.6 | 2.6 | 2.6 | 1.3 | 2.6 |
| Mexoryl ® SX | Terephthalylidene Dicamphor Sulfonic Acid | | | | 0.5 | | 1.0 | | | | | 0.5 |
| Sulisobenzone | Benzophenone-4 | 1.0 | | | | | | | | | | |
| Amino acid or amine base or hard base to neutralise Mexoryl ® SX and/or Sulisobenzone | | qs | | | qs | | qs | | | | | qs |
| Microfine UV attenuating Pigments | | | | | | | | | | | | |
| | Titanium Dioxide | 3.0 | 3.0 | 3.0 | 0.5 | | | 6.0 | 1.0 | | | 3.0 |
| | Zinc Oxide | | | | | | 3.0 | 6.0 | | | | |
| Tinosorb ® M | Methylene Bis-Benzotriazolyl Tetramethylbutylphenol | | | | 5.0 | 0.2 | | | | 2.0 | | |
| Other oil soluble components | | | | | | | | | | | | |
| PCL Liquid 100 | Cetearyl Octanoate | | | | | 3.0 | 3.0 | | | | | |
| Corapan TQ ® (Symrise) | Diethylhexyl 1,6-Naphthalate | | | | | | | | 3.0 | | 3.0 | |
| Dragoxat 89 (Symrise) | Ethylhexyl Isononoate | | | | 1.0 | 3.0 | | | | | | |
| Isoadipate | Diisopropyl Adipate | | | | 3.0 | 1.0 | 3.0 | | | | | |
| Isopropyl myristate (Symrise) | Isopropyl Myristate | | | | | | | | 2.0 | | 4.0 | |
| Neutral oil (Symrise) | Caprylic/Capric Triglyceride | | | | | | 2.0 | | 5.0 | 4.0 | | |
| Isodragol (Symrise) | Triisononanoin | | | | | | 1.0 | | 6.0 | | | |
| Cetiol OE (Cognis) | Dicaprylyl Ether | 2.0 | 2.0 | | | | 2.0 | 1.0 | 3.0 | | | |
| | Dicaprylyl Carbonate | | | 2.0 | | | 2.0 | | | | | |
| | Isohexadecane | | | | | | | | | | | 3.0 |
| Paraffin oil | Mineral Oil | | | | | | | | | 4.0 | | |
| Tegosoft TN ® (Goldschmidt) | C12-15 Alkyl Benzoate | 5.0 | 5.0 | 3.0 | 4.0 | 2.0 | | | 1.0 | 4.0 | 5.0 | 5.0 |
| Abil 100 ® (Goldschmidt) | Dimethicone | | | | 1.0 | | | | 2.0 | | 2.0 | 0.5 |
| Dow Corning ® 193 Fluid (Dow corning) | Peg-12 Dimethicone | | | | | | 1.0 | | | | | |
| | Cyclopentasiloxane | | | | | | | | | | | 5.0 |
| | Cetyl Dimethicone | | | | | | | | | 1.0 | | |
| | Hydrogenated Coco-Glycerides | 1.0 | 1.0 | | | | 1.0 | 0.5 | | | | |
| | Butylene Glycol Dicaprylate/Dicaprate | 1.0 | 1.0 | 4.0 | | | 1.0 | 7.5 | | | | |
| | Dibutyl Adipate | | | | 2.0 | | | | | | | |
| | Trimethoxycaprylylsilane | | | | | | 1.0 | | | | | |
| Lanette O ® (Cognis) | Cetearyl Alcohol | | | | 1.5 | | | | | | | |
| Lanette 16 ® (Cognis) | Cetyl Alcohol | | | | | | 1.0 | 1.0 | | 0.5 | 1.0 | |
| Lanette 18 ® (Cognis) | Stearyl Alcohol | 1.0 | 1.0 | 2.0 | | | 1.0 | | 4.5 | | | |
| alpha-Bisabolol (Symrise) | Bisabolol | | | | 0.2 | 0.1 | | | | | | |

-continued

| RAW MATERIAL NAME (MANUFACTURER) | INCI | 1 | 2 | 3 | 4 | 5 | 6 | 7 | 8 | 9 | 10 | 11 |
|---|---|---|---|---|---|---|---|---|---|---|---|---|
| Copherol 1250 ® (Cognis) | Tocopheryl Acetate | 0.5 | 0.5 | 0.5 | 0.5 | 0.5 | 0.5 | 0.5 | | 0.5 | | 0.5 |
| D-Panthenol (BASF) | Panthenol | | | 0.5 | | | 0.5 | | | 0.5 | | |
| | Retinyl-Palmitate | | | | | | | 0.5 | | | | |
| Frescolat ® ML | Menthyl Lactate | | | | | 0.5 | | | 0.5 | | | |
| Fragrance | Fragrance/Parfum | qs | qs | qs | qs | qs | qs | qs | qs | qs | | |
| | Creatinine | 0.05 | 0.05 | | | | | | | | | |
| EDTA BD ® (BASF) | Disodium-EDTA | 0.2 | 0.2 | 0.15 | 0.15 | 0.15 | 0.2 | 0.15 | 0.15 | 0.15 | 0.2 | 0.2 |
| Viscosity modifiers/ stability aids | | | | | | | | | | | | |
| Bentone Gel ® M IO V (Elementis Specialties) | Mineral Oil and Quaternium-Disteardimonium Hectorite and Propylene Carbonate | | | | | | | | | 0.5 | | |
| Carbopol Ulrez 10 (Noveon) | Carbomer | | | | | 0.10 | | | | 0.2 | | |
| Carbopol ETD 2001 (Noveon) | Carbomer | | | | 0.5 | | 0.1 | | | | | |
| Keltrol T ® (Calgon) | Xanthan Gum | 0.2 | 0.2 | 0.3 | 0.3 | 0.4 | 0.2 | 0.2 | | | 0.2 | 0.2 |
| Pemulen TR 2 (Novion) | Acrylates/C10-30 Alkyl Acrylate Crosspolymer | | | | | | | 0.2 | | 0.1 | | 0.1 |
| Veegum ultra ® (Vanderbilt) | Magnesium Aluminium Sulphate | 1.0 | 1.0 | | | 0.2 | 1.0 | | | | | |
| Aerosil 200 | Silica | | | | | | | | | 0.5 | 0.2 | |
| Film Forming Polymers | | | | | | | | | | | | |
| Antaron V-216/516 | VP/Hexadecene Copolymer | 0.5 | 0.5 | | | 2.0 | 0.5 | | | 1.0 | 1.0 | 2.0 |
| Antaron V-220 | VP/Eicosene Copolymer | | | | | | | | 2.0 | | | |
| Dermacryl 79 | Acrylates/Octylacrylamide Coploymer | | | | 2.0 | | 0.5 | | | | 1.0 | |
| Antaron WP-660 | Tricantonyl PVP | | | 1.0 | | | | 2.0 | | | | |
| Avalure UR 450/525 | PPG-17/IPDI/DMPA copolymer | | | | 1.0 | | 1.0 | | | | | |
| Other water soluble components | | | | | | | | | | | | |
| Water | Water (Aqua) | qs | qs | qs | qs | qs | qs | qs | qs | qs | qs | qs |
| Neutralisation base for acidic components such as carbomers, and/or stearic acid etc | | qs | qs | qs | qs | qs | qs | | qs | qs | qs | qs |
| Preservation agents | | qs | qs | qs | qs | qs | qs | qs | qs | qs | qs | qs |
| 1,3-Butylene glycol | 1,3-Butylene Glycol | | | | | 1.0 | | | | | | |
| Ethanol (96%) | Ethyl Alcohol | 3.0 | 3.0 | | | | 3.0 | 3.0 | 2.0 | | | |
| Glycerin 99% | Glycerin | 5.0 | 5.0 | 4.5 | | 0 | 5.0 | 3.0 | 5.0 | 3.0 | 3.0 | 4.0 |
| Hydrolite-5 (Symrise) | Pentylene Glycol | 5.0 | 5.0 | 3.0 | 3.0 | 2.0 | 5.0 | 4.0 | 3.0 | | | |
| Symdiol 68 | 1,2-hexylenediol and 1,2-Caprylyldiol | | | | 0.5 | | | | | | | |
| 1,2-Propylene glycol | Propylene Glycol | | | | | 1.0 | | | | 5.0 | | 5.0 |
| Soja extract | Glycine soja (soybean) germ extract | | | | 0.5 | | | | | 1.0 | 2.0 | 0.5 |
| | Sodium Ascorbyl Phosphate | | | | | 0.2 | | | | | | |
| DHA | Dihydroxyacetone | | | | | | 3.0 | | 5.0 | | | |
| Water soluble dyestuff | | Qs | qs | qs | qs | qs | qs | qs | qs | qs | qs | qs |
| Plant Extract(s) | | qs | qs | 5.00 | qs | qs | qs | qs | qs | 5.0 | qs | qs |

2. W/O Emulsions: SPF>20

| RAW MATERIAL NAME (MANUFACTURER) | INCI | 1 | 2 | 3 | 4 | 5 | 6 | 7 | 8 | 9 | 10 |
|---|---|---|---|---|---|---|---|---|---|---|---|
| Emulsifier | | | | | | | | | | | |
| | Polyglyceryl 2-Dipolyhydroxystearate | 4.0 | 5.0 | | | | | | | 3.0 | 2.5 |
| | PEG-45/Dodecyl Glycol Copolymer | | | | | 1.0 | | | | | |
| | Polyglyceryl 3-Polyricinoleate | | | | | | | | | 3.0 | 3.5 |
| | Cetyl PEG/PPG-10/1-Dimethicone | | | | | 1.5 | | | | | |
| | Lauryl PEG/PPG-18/18 Methicone | | | | | | | 3.0 | | | |
| | Cetearyl Alcohol, Peg-40 Castor Oil, Sodium Cetearyl Sulfate | | | | | | | | 3.75 | | |
| | PEG-30 Dipolyhydroxystearate | | | 3.5 | 3.5 | | 3.5 | 1.0 | | | |
| | Polyglyceryl-3 Methyl-glucose Distearate | | | | | 2.0 | | | 2.0 | | |
| | Sorbitan Stearate | | | | | | | | 1.0 | | |
| Oil Soluble UV Filters | | | | | | | | | | | |
| Neo Heliopan ® AV (Symrise) | Ethylhexyl Methoxy-cinnamate | 8.0 | 2.0 | | 2.0 | 3.0 | | | | | 5.0 |
| Neo Heliopan ® 303 (Symrise) | Octocrylene | 5.0 | 2.0 | 3.0 | 3.0 | 3.0 | 8.0 | | 5.0 | 10.0 | 3.0 |
| Neo Heliopan ® 357 (Symrise) | Butyl Methoxydibenzoyl-methane | 4.5 | 1.0 | 2.0 | 2.0 | 3.0 | 0.5 | 2.0 | 3.0 | 3.0 | |
| Neo Heliopan ® E 1000 (Symrise) | Isoamyl p-Methoxy-cinnamate | | 1.0 | 1.0 | 3.0 | | | | | | 5.0 |
| Neo Heliopan ® HMS (Symrise) | Homosalate | | 1.0 | 1.0 | 3.0 | 2.0 | | | | 3.0 | 3.0 |
| Neo Heliopan ® OS (Symrise) | Ethylhexyl Salicylate | | 1.0 | 1.0 | 3.0 | 3.0 | | | | 5.0 | 5.0 |
| Neo Heliopan ® MBC (Symrise) | 4-Methylbenzylidene-camphor | | 0.5 | | 0.5 | | | | | | 1.0 |
| Neo Heliopan ® MA (Symrise) | Menthyl Anthranilate | | 1.0 | | 0.5 | | | | | | |
| Neo Heliopan ® BB (Symrise) | Benzophenone-3 | | 1.0 | | 1.0 | | | 0.5 | 0.5 | | |
| Mexoryl ® XL | Drometrizole Trisiloxane | | 2.0 | | 3.0 | | 3.0 | | | | |
| Tinosorb ® S | Bis-Ethylhexyloxyphenol Methoxyphenyl Triazine | 1.0 | 0.5 | 2.5 | 0.5 | 3.0 | | | | 1.5 | 1.5 |
| Uvinul ® T-150 | Ethylhexyl Triazone | | 0.5 | 2.0 | 0.5 | 3.0 | 1.0 | | | 1.0 | 1.0 |
| | -Bis[5-1(dimethylpropyl)benzoxazol-2-yl-1.5 5 3 (4-phenyl)imino]-6-(2-ethylhexyl)imino-1,3,5-triazine | 0.5 | 0.5 | | 0.5 | | | | | | |
| Uvinul ® A Plus | Diethylamino Hydroxy-benzoyl Hexylbenzoate | 1.0 | 0.5 | 2.0 | 0.5 | 0.5 | | | | 1.0 | 1.0 |
| Indanylidene derivatives according to DE 10055940 | | | 0.5 | | 0.5 | | | | | | |
| Benzoylcinnamylnitrile derivatives according to WO 2006/015954 | | | 0.5 | | 0.5 | | | | | | |
| Parsol SLX | Polysiloxane-15 | | 1.0 | | 1.0 | | | | | | 3.0 |
| Uvasorb HEB | Diethylhexyl Butamido Triazone | 0.5 | 0.5 | | 0.5 | | | | | | |
| Benzylidene butyrolactones according to EP 1008593 | | | 0.5 | | 0.5 | | | | | | |
| Benzylidene-dicarbonyl compounds described in WO/2005/107692 | | | 0.5 | | 0.5 | | | | | | |

| RAW MATERIAL NAME (MANUFACTURER) | INCI | 1 | 2 | 3 | 4 | 5 | 6 | 7 | 8 | 9 | 10 |
|---|---|---|---|---|---|---|---|---|---|---|---|
| Water Soluble UV Filters | | | | | | | | | | | |
| Neo Heliopan ® AP (Symrise), neutralised with lysine or arginine or ornithine or histidine | Disodium Phenyl-dibenzimidazoletetra-sulphonate | 1.2 | 0.5 | 1.0 | 0.5 | 0.5 | | | 0.5 | | 0.8 |
| Neo Heliopan ® Hydro (Symrise) neutralised with lysine or arginine or ornithine or histidine | Phenylbenzimidazole-sulphonic Acid | 1.3 | 1.3 | 2.6 | 1.3 | 1.8 | 1.8 | 2.6 | 2.6 | 1.3 | 1.3 |
| Mexoryl SX | Terephthalylidene Dicamphor Sulfonic Acid | | 0.5 | | 0.5 | | 1.0 | | | | |
| Sulisobenzone | Benzophenone-4 | | | | | | | 1.0 | | | |
| Amino acid or amine base or hard base to neutralise Mexoryl SX and/or sulisobenzone | | | qs | | qs | | qs | qs | | | |
| Microfine UV attenuating Pigments | | | | | | | | | | | |
| | Titanium Dioxide | 3.0 | 3.0 | 3.0 | 3.0 | 3.0 | | 6.0 | 1.0 | 3.0 | 3.0 |
| | Zinc Oxide | | | | | | | 6.0 | | | |
| Tinosorb M | Methylene Bis-Benzotriazolyl Tetramethylbutylphenol | | 1.0 | | 1.0 | | | | | | 3.0 |
| Other oil soluble components | | | | | | | | | | | |
| PCL Liquid 100 | Cetearyl Octanoate | | | | | | | | | | |
| Corapan TQ ® (Symrise) | Diethylhexyl 1,6-Naphthalate | | | | | | | | 3.0 | | |
| Dragoxat 89 (Symrise) | Ethylhexyl Isononoate | | | | | 1.0 | | | | | |
| Isoadipate | Diisopropyl Adipate | | | 3.0 | 5.0 | 5.0 | | | | | |
| Isopropyl myristate (Symrise) | Isopropyl Myristate | 3.0 | | | | | | 2.0 | | 4.0 | |
| Neutral oil (Symrise) | Caprylic/Capric Triglyceride | | 5.0 | | 3.0 | | | 5.0 | | 4.0 | 4.0 |
| Isodragol (Symrise) | Triisononanoin | | | | | | | | 6.0 | | |
| | Isohexadecane | | | | | | 6.0 | | | | |
| | Dicaprylyl Carbonate | | | 5.0 | | | 8.0 | | | | |
| Cetiol OE (Cognis) | Dicaprylyl Ether | | 5.0 | | 5.0 | | | 1.0 | 3.0 | | |
| Paraffin oil | Mineral Oil | | | | | | | | | | |
| Tegosoft TN ® (Goldschmidt) | C12-15 Alkyl Benzoate | 10.0 | 10.0 | 10.0 | 4.0 | 9.0 | | | 1.0 | 5.0 | 5.0 |
| Abil 100 ® (Goldschmidt) | Dimethicone | | 1.0 | | 1.0 | | | | 2.0 | | |
| Dow Corning ® 193 Fluid (Dow corning) | PEG-12 Dimethicone | | | | | | 1.0 | | | | |
| | Cetyl Dimethicone | | | | 2.0 | | | | | 2.0 | 2.0 |
| | Cyclomethicone | | | | | 15 | | | | | |
| | Cyclohexasiloxane | | | | | | | 5.0 | | | |
| | Cyclopentasiloxane | | | | | | | 5.0 | | | |
| | Simethicone | | | | | | | | | 2.0 | 2.0 |
| | Hydrogenated Coco-Glycerides | | | | 1.0 | | | 0.5 | | | |
| | Butylene Glycol Dicaprylate/Dicaprate | 7.5 | 3.0 | | 3.0 | 8.0 | | 7.5 | | | |
| | Trimethoxycaprylylsilane | | | | | 0.2 | | | | | |
| Lanette 16 ® (Cognis) | Cetyl Alcohol | | | | | | | 1.0 | | 0.5 | 0.5 |
| Lanette 18 ® (Cognis) | Stearyl Alcohol | | | | | | | | 3.0 | | |
| alpha-Bisabolol (Symrise) | Bisabolol | | 0.2 | | 0.2 | 0.2 | | | | 0.1 | 0.1 |
| Copherol 1250 ® (Cognis) | Tocopheryl Acetate | 0.5 | 0.5 | 0.5 | 0.5 | 0.5 | 0.5 | 0.5 | | 0.5 | 0.5 |
| D-Panthenol (BASF) | Panthenol | 0.5 | 0.5 | 0.5 | 0.5 | 0.5 | 0.5 | 0.5 | | 0.5 | 0.5 |
| | Retinyl Palmitate | | | 0.5 | | | 0.5 | | | | |
| Fragrance | Fragrance/Parfum | qs | qs | qs | qs | qs | qs | qs | qs | qs | qs |
| | Creatinine | 0.05 | 0.05 | 0.05 | | | | | | | |
| | Taurine | | | 1.0 | | | | | | | |
| EDTA BD ® (BASF) | Disodium-EDTA | 0.2 | 0.2 | 0.15 | 0.15 | 0.15 | 0.2 | 0.15 | 0.15 | 0.15 | 0.15 |

| RAW MATERIAL NAME (MANUFACTURER) | INCI | 1 | 2 | 3 | 4 | 5 | 6 | 7 | 8 | 9 | 10 |
|---|---|---|---|---|---|---|---|---|---|---|---|
| Viscosity modifiers/ stability aids | | | | | | | | | | | |
| Bentone Gel ® M IO V (Elementis Specialties) | Mineral Oil and Disteardimonium Hectorite and Propylene Carbonate | | | | | | | | 0.5 | | |
| | Microcystalline Wax | | | | | | | | | 2.0 | 2.0 |
| | Beeswax | | | | 0.3 | | | | | | |
| | Tricontanyl PVP | | | | | | | | | 2.0 | 2.0 |
| Keltrol T ® (Calgon) | Xanthan Gum | | | | | | | | 0.2 | | |
| Pemulen TR 2 (Novion) | Acrylates/C10-30 Alkyl Acrylate Crosspolymer | | | | | 0.3 | | | 0.1 | | |
| Aerosil 200 | Sodium Starch Octenylsuccinate Silica | 0.5 | 0.5 | 0.4 | | | | | | | |
| | Magnesium Sulfate | 0.3 | 0.3 | 0.3 | | | | | | | |
| | Sodium Chloride | | | | | | 0.5 | 0.5 | | | |
| Other water soluble components | | | | | | | | | | | |
| Water | Water (Aqua) | qs | qs | qs | qs | qs | qs | qs | qs | qs | qs |
| Neutralisation base for acidic components such as carbomers, and/or stearic acid etc | | qs | qs | qs | qs | | qs | | qs | qs | qs |
| Preservation agents | | qs | qs | qs | qs | qs | qs | qs | qs | qs | qs |
| 1,3-Butylene glycol | 1,3-Butylene Glycol | 5.0 | 5.0 | 3.0 | 3.0 | | | | | | |
| Ethanol (96%) | Ethyl Alcohol | 2.0 | 2.0 | 2.0 | 3.0 | 3.0 | 10.0 | 3.0 | 2.0 | 4.0 | 4.0 |
| Glycerin 99% | Glycerin | 5.0 | 5.0 | 2.0 | 2.0 | 4.0 | 5.0 | 3.0 | 5.0 | 3.0 | 3.0 |
| Hydrolite-5 (Symrise) | Pentylene Glycol | 1.0 | 1.0 | 3.0 | 3.0 | 2.0 | | 2.0 | 4.0 | 3.0 | |
| Symdiol 68 | 1,2-hexylenediol and 1,2-Caprylyldiol | | | | 0.5 | 0.5 | 0.5 | | | | |
| 1,2-Propylene glycol | Propylene Glycol | | | | | | | 3.0 | | 5.0 | 5.0 |
| Soja extract | Glycine soja (soybean) germ extract | | | | 0.5 | 0.5 | | | | | |
| | Sodium Ascorbyl Phosphate | | | | 0.5 | 0.2 | 0.2 | | | | |
| Water soluble dyestuff | | qs | qs | qs | qs | qs | qs | qs | qs | qs | qs |
| Plant Extract(s) | | qs | qs | qs | qs | qs | qs | qs | qs | 5.0 | 5.0 |

3. Spray/Mousse Emulsions: SPF>20

| RAW MATERIAL NAME (MANUFACTURER) | INCI | 1 | 2 | 3 | 4 | 5 | 6 | 7 | 8 | 9 | 10 |
|---|---|---|---|---|---|---|---|---|---|---|---|
| Emulsifier | | | | | | | | | | | |
| | Polyglycery 2-Dipolyhydroxystearate | 3.0 | | | | | | | | | |
| | Disodium PEG-5 Lauryl Citrate Sulfosuccinate | 2.5 | | | | | | | | | |
| | Capryl/Capramidopropyl Betaine | 0.7 | | | | | | | | | |
| | Sodium Laureth Sulfate | 0.3 | | | | | | | | | |
| Emulgin B2 ® (Cognis) | Ceteareth-20 | | 1.5 | 1.5 | | | | | | 2.0 | |
| | Polyester-5 | | | | 2.5 | | | | | | |
| | Sorbitan Laurate | | | | | | 2.5 | | | | |
| | Polyglyceryl-10 Laurate | | | | | | 2.0 | | | | |
| | PPG-15 Stearyl Ether | | | | | | | 4.0 | | | |
| | Polyacrylate-3 | | | | | 1.0 | | | | | |
| | Stearyl Phosphate | | | | | | | | 2.5 | | |
| | Sorbitan Stearate | | | | | | | | | 0.5 | |
| | Stearic Acid | | | | | | | 1.0 | | 1.0 | |
| | PEG 40 Stearate | | | | | | | | | 1.0 | |
| Oil Soluble UV Filters | | | | | | | | | | | |
| Neo Heliopan ® AV (Symrise) | Ethylhexyl Methoxycinnamate | | 6.0 | | | | | | 5.0 | 6.0 | |
| Neo Heliopan ® 303 (Symrise) | Octocrylene | 5.0 | | 8.0 | 10.0 | 10.0 | 5.0 | 4.0 | | 4.0 | |

-continued

| RAW MATERIAL NAME (MANUFACTURER) | INCI | 1 | 2 | 3 | 4 | 5 | 6 | 7 | 8 | 9 | 10 |
|---|---|---|---|---|---|---|---|---|---|---|---|
| Neo Heliopan ® 357 (Symrise) | Butyl Methoxydibenzoyl-methane | 3.0 | 4.0 | 4.0 | 2.0 | 2.5 | 3.0 | 5.0 | | 2.0 | 3.0 |
| Neo Heliopan ® E 1000 (Symrise) | Isoamyl p-Methoxy-cinnamate | | | | | | | | 5.0 | | |
| Neo Heliopan ® HMS (Symrise) | Homosalate | | | 3.0 | 3.0 | 5.0 | 5.0 | | | 3.0 | |
| Neo Heliopan ® OS (Symrise) | Ethylhexyl Salicylate | | | 3.0 | 5.0 | 5.0 | 5.0 | 4.0 | | 3.0 | |
| Neo Heliopan ® MBC (Symrise) | 4-Methylbenzylidene-camphor | | | | | | | | | 0.5 | |
| Neo Heliopan ® MA (Symrise) | Menthyl Anthranilate | | | 2.0 | | | | | | | |
| Neo Heliopan ® BB (Symrise) | Benzophenone-3 | | | | | | | | 0.5 | | |
| Mexoryl ® XL | Drometrizole Trisiloxane | | | | 4.0 | 3.0 | | | | 2.0 | |
| Tinosorb ® S | Bis-Ethylhexyloxyphenol Methoxyphenyl Triazine | | 2.5 | 2.5 | 1.0 | 0.5 | | | 2.5 | 1.0 | 1.5 |
| Uvinul ® T-150 | Ethylhexyl Triazone | 1.0 | 3.0 | 1.0 | 1.0 | 0.5 | 2.0 | | 1.0 | 1.0 | |
| | -Bis[5-1(dimethylpropyl)benzoxazol-2-yl-1.5 5 3 (4-phenyl)imino]-6-(2-ethylhexyl)imino-1,3,5-triazine | | 1.0 | 1.0 | | | | | | 1.0 | |
| Uvinul ® A Plus | Diethylamino Hydroxybenzoyl Hexyl Benzoate | | 1.0 | 1.0 | | 0.5 | 1.0 | 0.5 | | 1.0 | |
| Indanylidene derivatives according to DE 10055940 | | | | | | | | | | 0.5 | |
| Benzoylcinnamylnitrile derivatives according to WO 2006/015954 | | | | | | | | | | 1.0 | |
| Parsol SLX | Polysiloxane-15 | 3.0 | | 2.0 | | 2.0 | | | | 1.0 | |
| Uvasorb HEB | Diethylhexyl Butamido Triazone | | | 1.0 | | 0.5 | | 1.0 | | 0.5 | 1.0 |
| Benzylidene butyrolactones according to EP 1008593 | | | | | | | | | | 1.0 | |
| Benzylidene-dicarbonyl compounds described in WO/2005/107692 | | | | | | | | | | 1.0 | |

Water Soluble UV Filters

| | | | | | | | | | | | |
|---|---|---|---|---|---|---|---|---|---|---|---|
| Neo Heliopan ® AP (Symrise), neutralised with lysine or arginine or ornithine or histidine | Disodium Phenyl-dibenzimidazoletetra-sulphonate | 0.8 | 1.8 | 1.8 | | | | | | 1.0 | |
| Neo Heliopan ® Hydro (Symrise) neutralised with lysine or arginine or ornithine or histidine | Phenylbenzimidazole-sulphonic Acid | 2.6 | 3.2 | 3.2 | 2.6 | 2.6 | 2.6 | 1.8 | 1.3 | 1.3 | 2.6 |
| Mexoryl SX | Terephthalylidene Dicamphor Sulfonic Acid | | | | 1.0 | 0.5 | | | | 0.5 | |
| Sulisobenzone | Benzophenone-4 | | | | | | 1.0 | | | | |
| Amino acid or amine base or hard base to neutralise Mexoryl SX and/or sulisobenzone | | | | | qs | qs | qs | | | Qs | |

Microfine UV attenuating Pigments

| | | | | | | | | | | | |
|---|---|---|---|---|---|---|---|---|---|---|---|
| | Titanium Dioxide | | | | 3.0 | | | | | 1.5 | |
| | Zinc Oxide | | | | | | 3.0 | | | 1.5 | |

-continued

| RAW MATERIAL NAME (MANUFACTURER) | INCI | 1 | 2 | 3 | 4 | 5 | 6 | 7 | 8 | 9 | 10 |
|---|---|---|---|---|---|---|---|---|---|---|---|
| Tinosorb ® M | Methylene Bis-Benzotriazolyl Tetramethylbutylphenol | | 3.0 | 3.0 | | | | | | 1.0 | |
| Other oil soluble components | | | | | | | | | | | |
| PCL Liquid 100 | Cetearyl Octanoate | | | | | | 10.0 | | | | |
| Corapan TQ ® (Symrise) | Diethylhexyl 1,6-Naphthalate | | | | | | | | 3.0 | | |
| | C18-36 Acid Triglyceride | | 1.0 | 2.0 | | | | | | 2.0 | |
| Neutral oil (Symrise) | Caprylic/Capric Triglyceride | 10 | | | | | | | 5.0 | | |
| Isodragol (Symrise) | Triisononanoin | | | | | | 2.0 | | | | |
| Cetiol OE (Cognis) | Dicaprylyl Ether | | | | | | 3.0 | | 1.0 | | |
| | Dicaprylyl Carbonate | | | 5.0 | 2.0 | | 2.0 | | 5.0 | 10.0 | |
| | Isohexadecane | | | | | | | 3.0 | | | |
| | Ethylhexylglycerin | | | | | | | | | | 0.5 |
| | Cetyl Ricinoleate | | | | | | | | | | 0.1 |
| Tegosoft TN ® (Goldschmidt) | C12-15 Alkyl Benzoate | 5.0 | | | 10.0 | 8.0 | 5.0 | | 7.0 | | |
| Abil 100 ® (Goldschmidt) | Dimethicone | | | | | | | | | | 4.0 |
| Dow Corning ® 193 Fluid (Dow corning) | PEG-12 Dimethiconel | | | | | | 1.0 | | | | |
| | Cyclohexasiloxane | | | | | 10.0 | | | | | |
| | Cyclopentasiloxane | | | | | | | 2.0 | | | |
| | Phenyl Trimethicone | | | | | 3.0 | | 2.0 | | | |
| | Cyclomethicone | | | | | | | 1.0 | 0.5 | | |
| | Butylene Glycol Dicaprylate/Dicaprate | | 8.0 | 8.0 | | | | | 7.5 | 8.0 | 10.0 |
| Lanette 16 ® (Cognis) | Cetyl Alcohol | | | | | | | | 1.0 | | 0.5 |
| alpha-Bisabolol (Symrise) | Bisabolol | | 0.3 | 0.3 | | 0.2 | 0.1 | | | 0.3 | |
| Copherol 1250 ® (Cognis) | Tocopheryl Acetate | | 0.5 | 0.5 | 0.5 | 0.5 | 0.5 | 0.5 | 0.5 | 0.5 | |
| D-Panthenol (BASF) | Panthenol | | 0.5 | 0.5 | 0.5 | | 0.5 | | 0.5 | 0.5 | |
| | Retinyl-Palmitate | | | | | | | | 0.5 | | |
| Frescolat ® ML | Menthyl Lactate | | | | | | 0.5 | | | | |
| Fragrance | Fragrance/Parfum | qs | qs | qs | qs | Qs | Qs | Qs | Qs | qs | Qs |
| | Taurine | | 1.0 | 1.0 | | | | | | 1.0 | 0.5 |
| | Creatinine | | 0.05 | 0.05 | | | | | | 0.05 | 0.05 |
| EDTA BD ® (BASF) | Disodium-EDTA | 0.2 | 0.2 | 0.2 | 0.15 | 0.15 | 0.15 | 0.2 | 0.15 | 0.2 | 0.15 |
| Viscosity modifiers/stability aids | | | | | | | | | | | |
| | Sodium Chloride | 0.5 | | | | | | | | | |
| Avicel PC 611 (FMC Corporation) | Microcystalline Cellulose and Cellulose Gum | | | | | | 0.80 | | | | |
| Keltrol T ® (Calgon) | Xanthan Gum | | | | | | | 0.3 | 0.2 | | |
| Pemulen TR 2 (Novion) | Acrylates/C10-30 Alkyl Acrylate Crosspolymer | | 0.2 | 0.2 | | 0.25 | | | 0.2 | 0.2 | |
| Film Forming Polymers | | | | | | | | | | | |
| Antaron V-216/516 | VP/Hexadecene Copolymer | | 0.5 | 0.5 | | | 2.0 | | | 0.5 | |
| Dermacryl 79 | Acrylates/Octylacrylamide Copolymer | | | | | | | | 1.0 | | |
| | Trimethylpentanediol adiopic acid glycerine copolymer | | | | | | | | 1.0 | | |
| Avalure UR 450/525 | PPG-17/IPDI/DMPA copolymer | | | 0.5 | | | | | | 0.5 | |
| Other water soluble components | | | | | | | | | | | |
| Water | Water (Aqua) | qs | qs | qs | qs | qs | Qs | Qs | Qs | Qs | Qs |
| Neutralisation base for acidic components such as carbomers, and/or stearic acid etc | | qs | qs | qs | qs | qs | Qs | Qs | | Qs | Qs |
| Preservation agents | | qs | qs | qs | qs | qs | Qs | Qs | Qs | Qs | Qs |
| 1,3-Butylene glycol | 1,3-Butylene Glycol | | | | | 3.0 | | | | | |
| Ethanol (96%) | Ethyl Alcohol | 5.0 | 3.0 | 3.0 | 4.0 | 12.0 | | 10.0 | | 5.0 | 5.0 |

-continued

| RAW MATERIAL NAME (MANUFACTURER) | INCI | 1 | 2 | 3 | 4 | 5 | 6 | 7 | 8 | 9 | 10 |
|---|---|---|---|---|---|---|---|---|---|---|---|
| Glycerin 99% | Glycerin | 3.0 | 5.0 | 5.0 | 4.5 | | 5.0 | | 5.0 | 3.0 | 3.0 |
| Hydrolite-5 (Symrise) | Pentylene Glycol | | 5.0 | 5.0 | 3.0 | | | | | 3.0 | |
| Symdiol 68 | 1,2-hexylenediol and 1,2-Caprylyldiol | | | | | | | | | 0.5 | |
| 1,2-Propylene glycol | Propylene Glycol | | | | 5.0 | | 1.0 | 1.0 | 2.0 | | |
| Soja extract | *Glycine soja* (soybean) germ extract | | | | 1.0 | 0.5 | | | | | |
| | Sodium Ascorbyl Phosphate | | | | | 0.2 | | | | | |
| DHA | Dihydroxyacetone | | | | | | | | | | |
| Water soluble dyestuff | | qs | qs | qs | qs | qs | Qs | Qs | Qs | Qs | Qs |
| Plant Extract(s) | | qs | qs | qs | qs | qs | Qs | Qs | Qs | Qs | Qs |
| Propellant | | | | | | | | | | | Qs |

4. Daily Protection Formulations

| RAW MATERIAL NAME (MANUFACTURER) | INCI | 1 | 2 | 3 | 4 | 5 | 6 | 7 | 8 | 9 |
|---|---|---|---|---|---|---|---|---|---|---|
| Emulsifier | | | | | | | | | | |
| Emulsiphos (Symrise) | Potassium Cetyl Phosphate, Hydrogenated Palm Glycerides | 1.5 | 1.5 | 1.5 | | | | | | |
| Dracorin CE | Glyceryl Stearate Citrate | | | | | | 2.5 | | | |
| | PPG-1 Trideceth-6 | | | | | | 0.5 | | | |
| | Sorbitan Oleate | | | | | | 0.5 | | | |
| | Sucrose stearate | | | | | | | | 0.8 | |
| Hostaceron AMPS | Ammonium Polyacrylamido tauramide | | | | | | | | | 2.0 |
| | Polyglyceryl-3 Methylglucose Distearate | | | | | | | 3.5 | | |
| | Sorbitan Stearate | | | | | | | | 2.0 | |
| | Glyceryl Stearate | | | | | | | | | |
| | Isostearic Acid | 1.0 | 1.0 | 1.0 | | | | | | |
| | Stearic Acid | | | | | 2.0 | | | 1.0 | 4.0 |
| | PEG 40 Stearate | | | | | | | | | 1.0 |
| | PEG 100 Stearate | | | | 0.2 | 2.0 | | | | |
| | PEG-4 Laurate | | | | | | | | 0.3 | |
| Lanette E ® (Cognis) | Sodium Cetearyl Sulphate | | | | | | | | | 0.5 |
| | Steareth-2 | | | | 0.2 | | | | | |
| | Steareth-21 | | | | 1.0 | | | | | |
| | Laureth-7 | | | | 0.75 | | | | | |
| Oil Soluble UV Filters | | | | | | | | | | |
| Neo Heliopan ® AV (Symrise) | Ethylhexyl Methoxy-cinnamate | 8.0 | | | | | 4.0 | 3.0 | 5.5 | 5.0 |
| Neo Heliopan ® 303 (Symrise) | Octocrylene | | 3.0 | 3.0 | 1.0 | 2.0 | | | | |
| Neo Heliopan ® 357 (Symrise) | Butyl Methoxydibenzoyl-methane | 2.0 | 2.0 | 2.0 | 2.0 | 2.0 | 2.0 | 1.5 | 2.0 | 1.0 |
| Neo Heliopan ® HMS (Symrise) | Homosalate | | 3.0 | 3.0 | | 5.0 | | | | |
| Neo Heliopan ® OS (Symrise) | Ethylhexyl Salicylate | | 3.0 | 3.0 | 4.0 | 5.0 | | | 3.0 | |
| Water Soluble UV Filters | | | | | | | | | | |
| Neo Heliopan ® AP (Symrise), neutralised with lysine or arginine or ornithine or histidine | Disodium Phenyl-dibenzimidazoletetra-sulphonate | | 0.8 | 0.8 | | | 0.8 | | | |
| Neo Heliopan ® Hydro (Symrise) neutralised with lysine or arginine or ornithine or histidine | Phenylbenzimidazole-sulphonic Acid | 2.8 | 2.8 | 2.8 | 1.8 | 2.64 | 1.8 | 1.3 | 2.9 | 1.3 |

-continued

| RAW MATERIAL NAME (MANUFACTURER) | INCI | 1 | 2 | 3 | 4 | 5 | 6 | 7 | 8 | 9 |
|---|---|---|---|---|---|---|---|---|---|---|
| Mexoryl SX | Terephthalylidene Dicamphor Sulfonic Acid | | | | | | | | | 0.5 |
| Sulisobenzone | Benzophenone-4 | | | | | 0.5 | | | | |
| Amino acid or amine base or hard base to neutralise Mexoryl SX and/or Sulisobenzone | | | | | | qs | | | | qs |
| Microfine UV attenuating Pigments | | | | | | | | | | |
| | Titanium Dioxide | | | | | 1.0 | 1.0 | | | |
| Other oil soluble components | | | | | | | | | | |
| Shea Butter | *Butyrospemum Parkii* | | | | | | | | | 2.0 |
| Corapan TQ ® (Symrise) | Diethylhexyl 1,6-Naphthalate | | | | | | | | | |
| Dragoxat 89 (Symrise) | Ethylhexyl Isononoate | 3.0 | 3.0 | 3.0 | | 3.0 | | | | |
| Isoadipate | Diisopropyl Adipate | | | | | | 3.0 | | | |
| Isopropyl myristate (Symrise) | Isopropyl Myristate | | | | | 5.0 | 5.0 | | | |
| | Tridecyl Trimellitate | | | | | | | 2.0 | | |
| | Myristyl Myristate | | | | | | | | 5.0 | |
| Neutral oil (Symrise) | Caprylic/Capric Triglyceride | | | | | | | 3.0 | 4.0 | |
| Cetiol OE (Cognis) | Dicaprylyl Ether | | | | | | 2.0 | | | |
| | Dicaprylyl Carbonate | 2.0 | 2.0 | 2.0 | | | | 3.0 | | |
| | Isohexadecane | | | | | | | | 8.0 | |
| | Ethylhexylglycerin | | | | | | 0.5 | | | |
| Paraffin oil | Mineral Oil | | | | | 2.0 | 0.5 | | | |
| Tegosoft TN ® (Goldschmidt) | C12-15 Alkyl Benzoate | | | | | | | 3.0 | | |
| Abil 100 ® (Goldschmidt) | Dimethicone | | | | | 1.0 | | 2.0 | | 1.0 |
| Dow Corning ® 193 Fluid (Dow corning) | PEG-12 Dimethicone | | | | | 1.0 | 1.0 | | | |
| | Hydrogenated Coco-Glycerides | | | | | | | 1.0 | 0.5 | |
| | Butylene Glycol Dicaprylate/Dicaprate | | | | | | | | 7.5 | |
| | Dibutyl Adipate | | | | | 2.0 | | | | |
| Lanette O ® (Cognis) | Cetearyl Alcohol | | | | | 1.5 | | | | |
| Lanette 16 ® (Cognis) | Cetyl Alcohol | 0.5 | 0.5 | 0.5 | 0.5 | 0.5 | 0.5 | 2.0 | 0.2 | |
| Lanette 18 ® (Cognis) | Stearyl Alcohol | | | | | 0.5 | 0.5 | | 4.5 | |
| | Myristyl Alcohol | | | | | | | | 1.0 | |
| Ceramide(s) | | | | | | | | | 0.5 | |
| alpha-Bisabolol (Symrise) | Bisabolol | | | | | 0.2 | 0.1 | 0.2 | 0.1 | |
| Copherol 1250 ® (Cognis) | Tocopheryl Acetate | 0.5 | 0.5 | 0.5 | 0.5 | 0.5 | 0.5 | 0.5 | 0.5 | 0.5 |
| D-Panthenol (BASF) | Panthenol | 1.0 | 1.0 | 1.0 | 0.5 | 0.5 | 0.5 | | 0.5 | 0.5 |
| | Retinyl Palmitate | 0.5 | 0.5 | 0.5 | | | | | 0.5 | |
| | Ubiquinone | 0.1 | | | | | | | | |
| Frescolat ® ML | Menthyl Lactate | 0.5 | | | | | | | | |
| Fragrance | Fragrance/Parfum | Qs | Qs | Qs | Qs | Qs | Qs | Qs | Qs | Qs |
| | Niacinamide | | 0.1 | | | 0.5 | 0.5 | | | |
| | Arbutin | | | 0.2 | | | | | | |
| 4-(1-Phenylethyl)1,3-benzenediol | | 0.2 | | | | 0.5 | | | | |
| | Kojic Acid | | | | 0.5 | | | | | |
| Liquorice extract | | | | | | | 0.5 | | | |
| | Glucosyl rutin + quercitrin | 0.1 | 0.1 | | | | 0.2 | | | |
| | Isoquercitrin | | | | | | 0.1 | | | |
| | Creatinine | 0.05 | | | | | | | | |
| EDTA BD ® (BASF) | Disodium-EDTA | 0.2 | 0.2 | 0.2 | 0.15 | 0.15 | 0.2 | 0.15 | 0.15 | 0.15 |

| RAW MATERIAL NAME (MANUFACTURER) | INCI | 1 | 2 | 3 | 4 | 5 | 6 | 7 | 8 | 9 |
|---|---|---|---|---|---|---|---|---|---|---|
| Viscosity modifiers/ stability aids | | | | | | | | | | |
| Carbopol Ultrez-10 (Noveon) | Carbomer | 0.15 | 0.15 | 0.15 | | 0.15 | 0.1 | | | 0.2 |
| Keltrol T ® (Calgon) | Xanthan Gum | 0.2 | 0.2 | 0.2 | | | | | 0.2 | |
| Pemulen TR 2 (Novion) | Acrylates/C10-30 Alkyl Acrylate Crosspolymer | | | | | | | 0.2 | | |
| Veegum ultra ® (Vanderbilt) | Magnesium Alaminium Silicate | | | | | | | | | 0.2 |
| Fucogel 1000 (Solabia) | Biosaccharide Gum-1 | | | | 0.2 | | | | | |
| Givobio GMg (Seppic) | Magnesium Gluconate | | | | | | 0.2 | | | |
| Sepigel 305 (Seppic) | Polyacrylamide and C13-14 Isoparaffin and Laureth-7 | | | | | | | | 3.0 | |
| Aerosil 200 | Silica | | | | | | | | | 0.3 |
| Other water soluble components | | | | | | | | | | |
| Water | Water (Aqua) | Qs | Qs | Qs | Qs | Qs | Qs | Qs | Qs | Qs |
| Neutralisation base for acidic components such as carbomers, and/or stearic acid etc | | Qs | Qs | Qs | Qs | Qs | Qs | Qs | Qs | Qs |
| Preservation agents | | Qs | Qs | Qs | Qs | Qs | Qs | Qs | Qs | Qs |
| 1,3-Butylene glycol | 1,3-Butylene Glycol | | | | | 1.0 | | 2.0 | 1.0 | 3.0 |
| Ethanol (96%) | Ethyl Alcohol | | | | | | | | | 3.0 |
| Glycerin 99% | Glycerin | | | | 5.0 | 5.00 | | 6.0 | 8.0 | |
| Hydrolite-5 (Symrise) | Pentylene Glycol | 5.0 | 5.0 | 5.0 | | 1.0 | | | | |
| Symdiol 68 | 1,2-hexylenediol and 1,2-Caprylyldiol | 0.5 | 0.5 | 0.5 | 0.5 | | | | | |
| 1,2-Propylene glycol | Propylene Glycol | | | | | | | 1.0 | | |
| Soja extract | *Glycine soja* (soybean) germ extract | 1.0 | | | | | | | 1.0 | |
| Peptides | | 0.3 | 0.3 | | 0.3 | 0.3 | | | | |
| | Sodium PCA | | | | | | | | 0.5 | |
| | Saccharomyces Ferment | | | | | | | | 0.3 | |
| | Ascorbyl Glucoside | | | | | | | | | 0.5 |
| Sodium or Magnesium Ascorbyl Phosphate | | 0.5 | 0.5 | 0.5 | | | | | | |
| DHA | Dihydroxyacetone | | | | 5.0 | | | | 5.0 | |
| Water soluble dyestuff | | Qs | Qs | Qs | Qs | Qs | Qs | Qs | Qs | Qs |
| Plant Extract(s) | | Qs | Qs | Qs | Qs | Qs | Qs | Qs | Qs | 5.0 |

The invention claimed is:

1. A method for preventing or delaying crystallization of phenylbenzimidazole sulfonic acid in a formulation comprising neutralizing phenylbenzimidazole sulfonic acid with a basic amino acid to a pH of 5.5 to 7.0, wherein a formulation comprising the neutralized phenylbenzimidazole sulfonic acid and having a pH of 5.5 to 7.0 remains free of phenylbenzimidazole sulfonic acid crystals after storage of the formulation at 20° C. for two or more days.

2. A method for enhancing UV absorption comprising combining phenylbenzimidazole sulfonic acid and one or more basic amino acids with one or more additional UV absorbers in a formulation to have a pH of from 5.5 to 7.0 wherein said formulation remains free of phenylbenzimidazole sulfonic acid crystals after storage of the formulation at 20° C. for two or more days.

3. The method according to claim 1, wherein the pH is from 6.0 to 6.8.

4. The method according to claim 2, wherein the pH is from 6.0 to 6.8.

5. The method according to claim 1, wherein the basic amino acid is selected from the group consisting of arginine, lysine, histidine and ornithine.

6. The method according to claim 1, wherein the formulation comprising the neutralized phenylbenzimidazole sulfonic acid remains free of phenylbenzimidazole sulfonic acid crystals after storage of the formulation at 20° C. for five or more days.

7. The method according to claim 1, further comprising adding at least one inorganic pigment to the neutralized phenylbenzimidazole sulfonic acid with a basic amino acid.

8. The method according to claim 7, wherein the at least one inorganic pigment is an X-ray-amorphous oxide pigment.

9. The method according to claim 1, further comprising adding at least one anionic, cationic, nonionic and/or amphoteric surfactant to the neutralized phenylbenzimidazole sulfonic acid with a basic amino acid.

10. The method according to claim 2, wherein the basic amino acid is selected from the group consisting of arginine, lysine, histidine and ornithine.

11. The method according to claim 2, further comprising adding at least one inorganic pigment to the neutralized phenylbenzimidazole sulfonic acid with a basic amino acid.

12. The method according to claim 11, wherein the at least one inorganic pigment is an X-ray-amorphous oxide pigment.

13. The method according to claim 2, further comprising adding at least one anionic, cationic, nonionic and/or amphoteric surfactant to the neutralized phenylbenzimidazole sulfonic acid with a basic amino acid.

14. The method according to claim 2, wherein the one or more UV absorbers are selected from the group consisting of p-aminobenzoic acid, 3-(4'-trimethylammonium)benzylidenebornan-2-one methyl sulphate, homomethyl salicylate, terephthalylidenedibornanesulphonic acid and its salts, 4-tert-butyl-4'-methoxydibenzoylmethane, 3-(4'-sulpho) benzylidenebornan-2-one and its salts, 2-ethylhexyl 2-cyano-3,3-diphenylacrylate, N-[(2 and 4)-[2-(oxoborn-3-ylidene) methyl]benzyl] acrylamide polymer, 2-ethylhexyl p-methoxycinnamate, ethyl p-aminobenzoate (25 mol) ethoxylated, isoamyl p-methoxycinnamate, 2,4,6-trianilino (p-carbo-2'-ethylhexyl-1'-oxy)-1,3,5-triazine, phenol-1,2-(2H-benzotriazol-2-yl)-4-methyl-6-(2-methyl-3-(1,3,3,3-tetramethyl-1-(trimethylsilyl)oxy)disiloxyanyl)propyl), 4,4'-[(6-[4-(1,1-dimethyl) aminocarbonyl)phenylamino]-1,3,5-triazin-2,4-diyl)-diimino]bis(benzoicacid 2-ethylhexyl ester), 3-(4'-methylbenzylidene)-d,l-camphor, 3-benzylidenecamphor, 2-ethylhexyl salicylate, 2-ethylhexyl 4-dimethylaminobenzoate, hydroxy-4-methoxybenzophenone, 2-hydroxy-4-methoxybenzophenone-5-sulphonic acid and its salts, 2,2'-methylenebis(6-(2H-benzotriazol-2-yl)-4-1,1,3,3-tetramethylbutyl)-phenol), phenylenebisbenzimidazyltetrasulphonic acid disodium salt, 2,4-bis[{(4-(2-ethylhexyloxy)-2-hydroxy}phenyl]-6-(4-methoxyphenyl)-1,3,5-triazine, benzylidenemalonate-polysiloxane menthyl anthranilate, hexyl 2-(4-diethylamino-2-hydroxybenzoyl) benzoate, indanylidene compounds, benzoylcinnamyl nitriles, benzylidene butyrolactones, and benzylidene-β-dicarbonyl compounds.

\* \* \* \* \*

UNITED STATES PATENT AND TRADEMARK OFFICE
CERTIFICATE OF CORRECTION

PATENT NO. : 8,440,172 B2  
APPLICATION NO. : 12/668152  
DATED : May 14, 2013  
INVENTOR(S) : William Johncock et al.

Page 1 of 1

It is certified that error appears in the above-identified patent and that said Letters Patent is hereby corrected as shown below:

In the Claims:

At column 66, claim number 14, line number 1, should read as follows:

(p-carbo-2'-ethylhexyl-1'-oxy)-1,3,5-triazine, ~~phenol-1,2-~~ phenol,2-

Signed and Sealed this  
Twentieth Day of August, 2013

Teresa Stanek Rea  
*Acting Director of the United States Patent and Trademark Office*